US006496719B2

(12) United States Patent
Hayashi

(10) Patent No.: US 6,496,719 B2
(45) Date of Patent: Dec. 17, 2002

(54) APPARATUS FOR DISPLAYING FLUORESCENCE IMAGES

(75) Inventor: Katsumi Hayashi, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 179 days.

(21) Appl. No.: 09/742,402

(22) Filed: Dec. 22, 2000

(65) Prior Publication Data

US 2001/0007921 A1 Jul. 12, 2001

(30) Foreign Application Priority Data

Dec. 24, 1999 (JP) .......................................... 11-366667

(51) Int. Cl.[7] .............................................. A61B 1/07
(52) U.S. Cl. ...................................... 600/478; 600/160
(58) Field of Search ................................ 600/476, 477, 600/478, 160; 250/458.1; 356/317

(56) References Cited

U.S. PATENT DOCUMENTS 6,070,096 A * 5/2000 Hayashi ...................... 600/477

6,422,994 B1 * 7/2002 Kaneko et al. ............. 600/160

* cited by examiner

Primary Examiner—Peter Nerbun
(74) Attorney, Agent, or Firm—Sughrue Mion, PLLC

(57) ABSTRACT

A complementary color filter transmits only fluorescence components of fluorescence having been produced from a measuring site exposed to excitation light, which fluorescence components have wavelengths falling within a wavelength region acting as a complementary color with respect to a desired wavelength region. A complementary color signal intensity detector detects a signal intensity of the fluorescence components having passed through the complementary color filter. An entire signal intensity detector detects a signal intensity of fluorescence components, which have wavelengths falling within an entire measurement wavelength region. A signal intensity of fluorescence components, which have wavelengths falling within the desired wavelength region, is calculated from the signal intensities detected by the complementary color signal intensity detector and the entire signal intensity detector. Image information in accordance with the thus calculated signal intensity is displayed.

5 Claims, 8 Drawing Sheets

F I G. 2
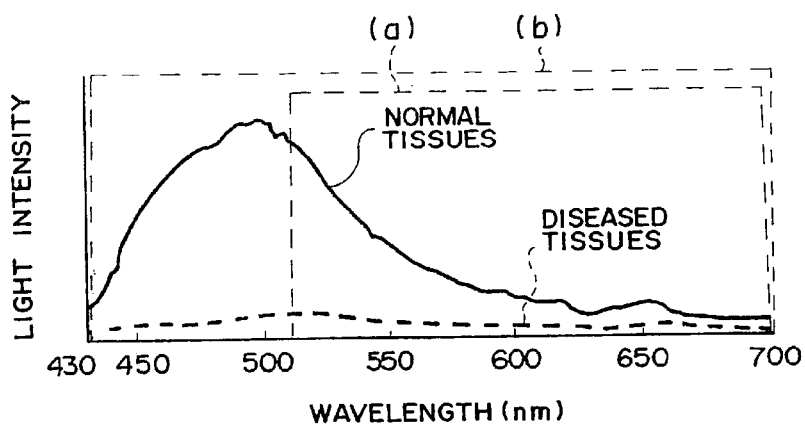
F I G. 3
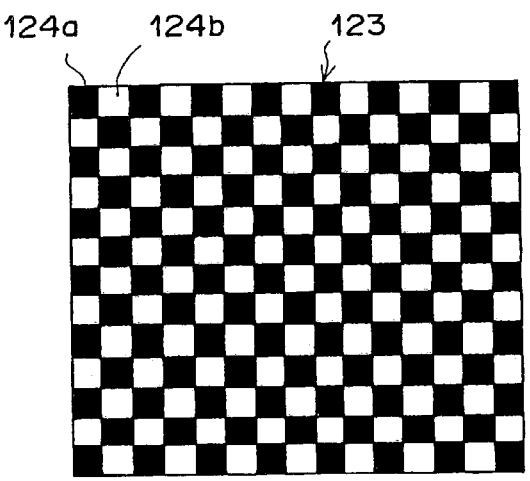
F I G. 4
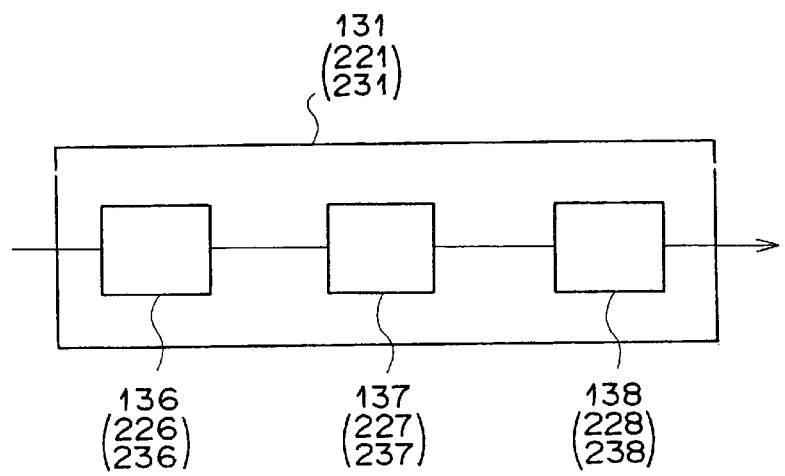

F I G. 5
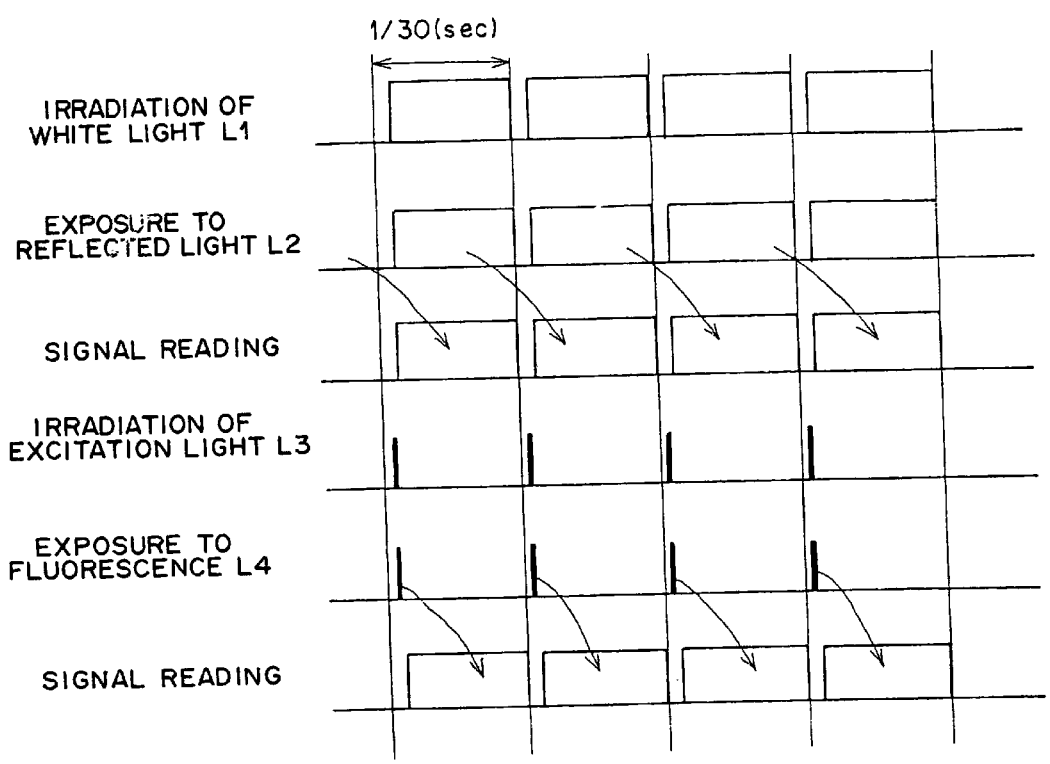

APPARATUS FOR DISPLAYING FLUORESCENCE IMAGES

BACKGROUND OF THE INVENTION

1. Field of the Invention

This invention relates to an apparatus for displaying a fluorescence image, wherein a fluorescence image in accordance with characteristics of fluorescence, which is produced from a measuring site in a living body when the measuring site is exposed to excitation light, is displayed.

2. Description of the Related Art

There have heretofore been proposed apparatuses for displaying a fluorescence image, wherein location and an infiltration range of diseased tissues are displayed as an image by the utilization of characteristics such that, in cases where excitation light having wavelengths falling within an excitation wavelength range for an intrinsic dye in a living body is irradiated to the living body, a pattern of a fluorescence spectrum of fluorescence produced by the intrinsic dye in the living body varies for normal tissues and diseased tissues.

FIG. 12 shows typical fluorescence spectra of the fluorescence produced from normal tissues and the fluorescence produced from diseased tissues, which fluorescence spectra have been measured by the inventors. It is assumed that the thus produced fluorescence results from superposition of the fluorescence produced by various kinds of intrinsic dyes in the living body, such as FAD, collagen, fibronectin, and porphyrin.

With the proposed apparatuses for displaying a fluorescence image, basically, fluorescence components of the fluorescence, which has been produced from a measuring site in the living body when the excitation light is irradiated to the measuring site, are detected via each of a plurality of band-pass filters, and the fluorescence components having wavelengths falling within desired wavelength regions are thereby selected. Also, signal intensities of the thus selected fluorescence components are detected. Thereafter, information in accordance with the detected signal intensities is displayed as a fluorescence image on a monitor, or the like. Therefore, a person who sees the displayed information is capable of recognizing the state of the diseased tissues. In many cases, the apparatuses for displaying a fluorescence image take on the form built in endoscopes, which are inserted into the body cavities, colposcopes, operating microscopes, or the like.

Ordinarily, as a combination of wavelength regions of the fluorescence components to be selected from the fluorescence, a combination of a red wavelength region and a blue wavelength region, at which the difference between the pattern of the fluorescence spectrum obtained from normal tissues and the pattern of the fluorescence spectrum obtained from diseased tissues occurs markedly, or a combination of an entire measurement wavelength region, from which a large amount of light is capable of being obtained, and the blue wavelength region, or the like, has heretofore been selected. For example, in cases where the combination of the red wavelength region and the blue wavelength region is to be selected, a mosaic filter constituted of a combination of band-pass filters, which transmit only the fluorescence components having wavelengths falling within the red wavelength region, and band-pass filters, which transmit only the fluorescence components having wavelengths falling within the blue wavelength region, has heretofore been located at a front surface of an image sensor. In this manner, the fluorescence components having wavelengths falling within the red wavelength region and the fluorescence components having wavelengths falling within the blue wavelength region have heretofore been detected. In cases where the combination of the entire measurement wavelength region and the blue wavelength region is to be selected, a mosaic filter constituted of a combination of blank areas, which transmit the fluorescence components having wavelengths falling within the entire measurement wavelength region, and the band-pass filters, which transmit only the fluorescence components having wavelengths falling within the blue wavelength region, has heretofore been utilized.

However, the fluorescence, which is produced from the living body tissues when the living body tissues are exposed to the excitation light, is weak. With the conventional apparatuses for displaying a fluorescence image described above, the fluorescence components having wavelengths falling within a desired wavelength region are selected from the weak fluorescence by use of the band-pass filter, which transmits only the fluorescence components having wavelengths falling within a primary color wavelength region, such as the red wavelength region or the blue wavelength region. Therefore, the conventional apparatuses for displaying a fluorescence image described above have the problems in that the efficiency, with which the fluorescence is utilized, cannot be kept high, adverse effects of photon noise, and the like, are apt to occur during photoelectric conversion, and a signal-to-noise ratio of the fluorescence image cannot be kept high.

SUMMARY OF THE INVENTION

The primary object of the present invention is to provide an apparatus for displaying a fluorescence image, wherein an efficiency, with which fluorescence having been produced from a measuring site in a living body exposed to excitation light, is utilized, is enhanced, and a signal-to-noise ratio of a displayed fluorescence image is kept high.

Another object of the present invention is to provide an apparatus for displaying a fluorescence image, wherein a fluorescence image is capable of being displayed in a real time mode, and a reliability of the displayed fluorescence image is capable of being enhanced.

The present invention provides a first apparatus for displaying a fluorescence image, comprising:

i) excitation light irradiating means for irradiating excitation light to a measuring site in a living body, the excitation light causing the measuring site to produce fluorescence, ii) image information acquiring means for acquiring image information in accordance with a signal intensity of fluorescence components of the fluorescence having been produced from the measuring site exposed to the excitation light, which fluorescence components have wavelengths falling within at least one desired wavelength region, and iii) displaying means for displaying the acquired image information, wherein the image information acquiring means comprises:

a) a complementary color filter for transmitting only fluorescence components of the fluorescence, which fluorescence components have wavelengths falling within a wavelength region acting as a complementary color with respect to the desired wavelength region, b) complementary color signal intensity detecting means for detecting a signal intensity of the fluorescence components of the fluorescence, which fluorescence components have passed through the complementary color filter, c) entire signal intensity detecting means for detecting a signal intensity of fluorescence components of the fluorescence, which fluorescence components have wavelengths falling within an entire measurement wavelength region of the fluorescence, and d) signal intensity calculating means for calculating the signal intensity of the fluorescence components of the fluorescence, which fluorescence components have wavelengths falling within the desired wavelength region, from the signal intensity, which has been detected by the complementary color signal intensity detecting means, and the signal intensity, which has been detected by the entire signal intensity detecting means.

In the first apparatus for displaying a fluorescence image in accordance with the present invention, the entire signal intensity detecting means should preferably comprise an all-pass filter for transmitting the fluorescence components of the fluorescence, which fluorescence components have wavelengths falling within the entire measurement wavelength region of the fluorescence, and entire measurement signal intensity detecting means for detecting the signal intensity of the fluorescence components of the fluorescence, which fluorescence components have passed through the all-pass filter.

In such cases, a plurality of complementary color filters and a plurality of all-pass filters should preferably be arrayed alternately on a two-dimensional plane so as to constitute a mosaic filter.

The present invention also provides a second apparatus for displaying a fluorescence image, comprising:

i) excitation light irradiating means for irradiating excitation light to a measuring site in a living body, the excitation light causing the measuring site to produce fluorescence, ii) image information acquiring means for acquiring image information in accordance with a signal intensity of fluorescence components of the fluorescence having been produced from the measuring site exposed to the excitation light, which fluorescence components have wavelengths falling within at least one desired wavelength region selected from among a blue wavelength region, a green wavelength region, and a red wavelength region, and iii) displaying means for displaying the acquired image information, wherein the image information acquiring means comprises:

a) a yellow filter for transmitting only fluorescence components of the fluorescence, which fluorescence components have wavelengths falling within a yellow wavelength region acting as a complementary color with respect to the blue wavelength region, b) a magenta filter for transmitting only fluorescence components of the fluorescence, which fluorescence components have wavelengths falling within a magenta wavelength region acting as a complementary color with respect to the green wavelength region, c) a cyan filter for transmitting only fluorescence components of the fluorescence, which fluorescence components have wavelengths falling within a cyan wavelength region acting as a complementary color with respect to the red wavelength region, d) complementary color signal intensity detecting means for detecting a signal intensity of the fluorescence components of the fluorescence, which fluorescence components have passed through the yellow filter, a signal intensity of the fluorescence components of the fluorescence, which fluorescence components have passed through the magenta filter, and a signal intensity of the fluorescence components of the fluorescence, which fluorescence components have passed through the cyan filter, e) entire signal intensity calculating means for calculating a signal intensity of fluorescence components of the fluorescence, which fluorescence components have wavelengths falling within an entire measurement wavelength region of the fluorescence, from the signal intensity of the fluorescence components having wavelengths falling within the yellow wavelength region, the signal intensity of the fluorescence components having wavelengths falling within the magenta wavelength region, and the signal intensity of the fluorescence components having wavelengths falling within the cyan wavelength region, which signal intensities have been detected by the complementary color signal intensity detecting means, and f) signal intensity calculating means for calculating the signal intensity of the fluorescence components of the fluorescence, which fluorescence components have wavelengths falling within the desired wavelength region, from the signal intensities, which have been detected by the complementary color signal intensity detecting means, and the signal intensity of the fluorescence components having wavelengths falling within the entire measurement wavelength region of the fluorescence, which signal intensity has been calculated by the entire signal intensity calculating means.

In the second apparatus for displaying a fluorescence image in accordance with the present invention, a plurality of yellow filters, a plurality of magenta filters, and a plurality of cyan filters should preferably be arrayed alternately on a two-dimensional plane so as to constitute a mosaic filter.

In the first and second apparatuses for displaying a fluorescence image in accordance with the present invention, the image information acquiring means may employ one of various techniques for acquiring the image information. For example, the image information acquiring means may employ a technique for acquiring the image information in accordance with the signal intensity of the fluorescence components of the fluorescence, which fluorescence components have wavelengths falling within only one desired wavelength region. Alternatively, the image information acquiring means may employ a technique for acquiring the image information in accordance with a ratio among the signal intensities of the fluorescence components of the fluorescence, which fluorescence components have wavelengths falling within a plurality of desired wavelength regions.

Also, in the first and second apparatuses for displaying a fluorescence image in accordance with the present invention, the displaying means may employ one of various displaying techniques. For example, in cases where the image information acquiring means acquires the image information in accordance with the ratio among the signal intensities of the fluorescence components of the fluorescence, which fluorescence components have wavelengths falling within the plurality of the desired wavelength regions, the ratio among the signal intensities may be displayed on a monitor, with a printer, or the like. Alternatively, a tint of a display color or luminance may be altered in accordance with the ratio among the signal intensities.

The term "all-pass filter" as used herein also includes a blank area for transmitting the fluorescence components of the fluorescence, which fluorescence components have wavelengths falling within the entire wavelength region of the fluorescence.

With the first apparatus for displaying a fluorescence image in accordance with the present invention, the signal intensity of the fluorescence components, which have wavelengths falling within the desired wavelength region, is calculated from the signal intensity of the fluorescence components, which have wavelengths falling within the wavelength region acting as the complementary color with respect to the desired wavelength region, and the signal intensity of the fluorescence components, which have wavelengths falling within the entire measurement wavelength region of the fluorescence. Therefore, the efficiency, with which the fluorescence having been produced from the measuring site is utilized, is capable of being enhanced. Accordingly, adverse effects of noise are capable of being reduced, and the signal-to-noise ratio of the displayed fluorescence image is capable of being kept high.

Also, with the first apparatus for displaying a fluorescence image in accordance with the present invention, wherein the signal intensity of the fluorescence components, which have wavelengths falling within the desired wavelength region, is calculated from the signal intensity of the fluorescence components, which have passed through the all-pass filter for transmitting the fluorescence components having wavelengths falling within the entire measurement wavelength region of the fluorescence, the fluorescence having been produced from the measuring site is capable of being utilized most efficiently, and the signal-to-noise ratio of the displayed fluorescence image is capable of being enhanced even further.

The second apparatus for displaying a fluorescence image in accordance with the present invention is provided with the yellow filter for transmitting only the fluorescence components, which have wavelengths falling within the yellow wavelength region acting as the complementary color with respect to the blue wavelength region, the magenta filter for transmitting only the fluorescence components, which have wavelengths falling within the magenta wavelength region acting as the complementary color with respect to the green wavelength region, and the cyan filter for transmitting only the fluorescence components, which have wavelengths falling within the cyan wavelength region acting as the complementary color with respect to the red wavelength region. Also, the signal intensity of the fluorescence components, which have wavelengths falling within the entire measurement wavelength region of the fluorescence, is calculated from the signal intensity of the fluorescence components, which have passed through the yellow filter, the signal intensity of the fluorescence components, which have passed through the magenta filter, and the signal intensity of the fluorescence components, which have passed through the cyan filter. Thereafter, the signal intensity of the fluorescence components, which have wavelengths falling within the at least one desired wavelength region selected from among the blue wavelength region, the green wavelength region, and the red wavelength region, is calculated from the signal intensity of the fluorescence components, which have passed through the yellow filter, the signal intensity of the fluorescence components, which have passed through the magenta filter, the signal intensity of the fluorescence components, which have passed through the cyan filter, and the signal intensity of the fluorescence components, which have wavelengths falling within the entire measurement wavelength region of the fluorescence. Therefore, the efficiency, with which the fluorescence having been produced from the measuring site is utilized, is capable of being enhanced. Accordingly, adverse effects of noise are capable of being reduced, and the signal-to-noise ratio of the displayed fluorescence image is capable of being kept high. Further, the three kinds of the filters are capable of being utilized also as color filters for acquiring ordinary color images, and therefore the cost of the apparatus for displaying a fluorescence image is capable of being kept low.

With the first apparatus for displaying a fluorescence image in accordance with the present invention, wherein the plurality of the complementary color filters and the plurality of the all-pass filters are arrayed alternately on a two-dimensional plane so as to constitute the mosaic filter, or with the second apparatus for displaying a fluorescence image in accordance with the present invention, wherein the plurality of the yellow filters, the plurality of the magenta filters, and the plurality of the cyan filters are arrayed alternately on a two-dimensional plane so as to constitute the mosaic filter, the signal intensity of the fluorescence components, which have wavelengths falling within the desired wavelength region, is capable of being calculated from the signal intensities of the fluorescence components having wavelengths falling within the respective wavelength regions, which signal intensities have been detected simultaneously. Therefore, the fluorescence image is capable of being displayed in the real time mode, and the reliability of the displayed fluorescence image is capable of being enhanced.

BRIEF DESCRIPTION OF THE DRAWINGS

FIG. 2 is a graph showing transmission wavelength regions of band-pass filters constituting a mosaic filter for a fluorescence image employed in the endoscope system, in which the first embodiment of the apparatus for displaying a fluorescence image in accordance with the present invention is employed, FIG. 3 is a schematic view showing the mosaic filter for a fluorescence image employed in the endoscope system, in which the first embodiment of the apparatus for displaying a fluorescence image in accordance with the present invention is employed, FIG. 4 is a block diagram showing a signal processing circuit employed in the endoscope system, in which the first embodiment of the apparatus for displaying a fluorescence image in accordance with the present invention is employed, FIG. 5 is a timing chart employed in the endoscope system, in which the first embodiment of the apparatus for displaying a fluorescence image in accordance with the present invention is employed.

DESCRIPTION OF THE PREFERRED EMBODIMENTS

The present invention will hereinbelow be described in further detail with reference to the accompanying drawings.

Figure 1:
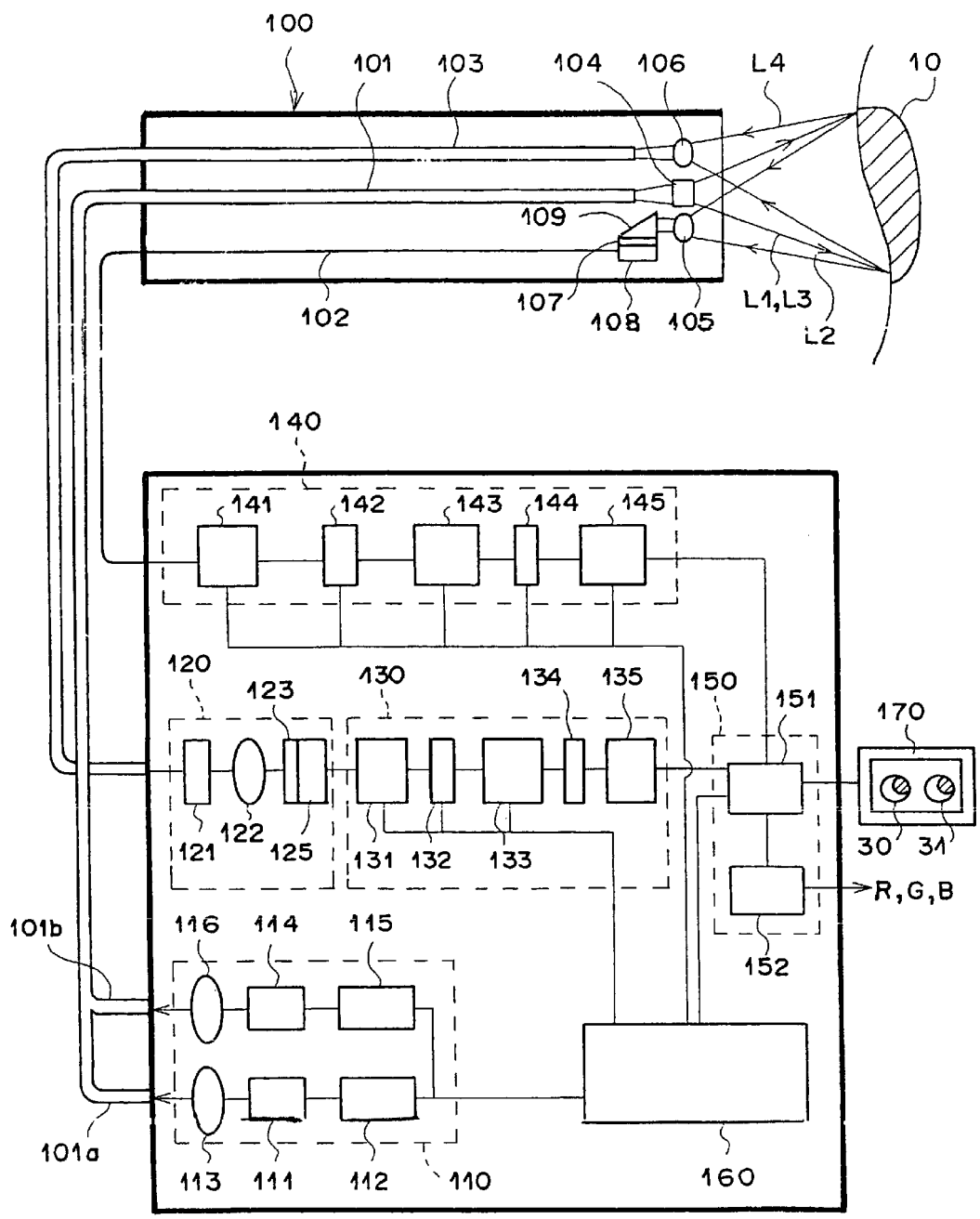
FIG. 1 is a schematic view showing an endoscope system, in which a first embodiment of the apparatus for displaying a fluorescence image in accordance with the present invention is employed.

Firstly, an endoscope system, in which a first embodiment of the apparatus for displaying a fluorescence image in accordance with the present invention is employed, will be described hereinbelow with reference to FIG. 1 to FIG. 5. FIG. 1 is a schematic view showing the endoscope system, in which the first embodiment of the apparatus for displaying a fluorescence image in accordance with the present invention is employed. In the endoscope system, in which the first embodiment of the apparatus for displaying a fluorescence image in accordance with the present invention is employed, excitation light is irradiated to a measuring site in a living body, the excitation light causing the measuring site to produce fluorescence. The fluorescence produced from the measuring site is two-dimensionally acquired as a fluorescence image and with an image fiber. The fluorescence image is detected by a charge coupled device (CCD) image sensor combined with a mosaic filter constituted of an array of yellow filters for transmitting only fluorescence components of the fluorescence, which fluorescence components have wavelengths falling within a wavelength region of at least 510 nm, and blank areas for transmitting fluorescence components of the fluorescence, which have wavelengths falling within an entire measurement wavelength region. In this manner, signal intensity of the fluorescence components of the fluorescence, which fluorescence components have wavelengths falling within the wavelength region of at least 510 nm, and signal intensity of the fluorescence components of the fluorescence, which fluorescence components have wavelengths falling within the entire measurement wavelength region, are detected. Further, signal intensity of fluorescence components of the fluorescence, which fluorescence components have wavelengths falling within a blue wavelength region of at most 510 nm, is calculated from the thus detected two signal intensities. Thereafter, image information is displayed on a monitor as a pseudo color image in accordance with a ratio between the signal intensity of fluorescence components of the fluorescence, which fluorescence components have wavelengths falling within the blue wavelength region, and the signal intensity of the fluorescence components of the fluorescence, which fluorescence components have wavelengths falling within the entire measurement wavelength region.

The endoscope system, in which the first embodiment of the apparatus for displaying fluorescence information in accordance with the present invention is employed, comprises an endoscope 100 to be inserted into a region of a patient, which region is considered as being a diseased part, and an illuminating unit 110 provided with light sources for producing white light, which is used when an ordinary image is to be displayed, and the excitation light, which is used when a fluorescence image is to be displayed. The endoscope system also comprises a fluorescence imaging unit 120 for receiving the fluorescence, which is produced from the measuring site in the living body when the measuring site is exposed to the excitation light, and detecting the image of the fluorescence. The endoscope system further comprises a fluorescence image processing unit 130 for performing image processing for displaying the fluorescence image as a pseudo color image in accordance with the ratio between signal intensities of fluorescence components of the fluorescence, which fluorescence components have wavelengths falling within predetermined wavelength regions. The endoscope system still further comprises an ordinary image processing unit 140 for performing image processing for displaying an ordinary image as a color image. The endoscope system also comprises a display image processing unit 150 for superimposing the color image of the ordinary image and the pseudo color image of the fluorescence image one upon the other. The endoscope system further comprises a controller 160, which is connected to the respective units and controls operation timings. The endoscope system still further comprises a monitor 170 for displaying the ordinary image (specifically, the color image of the ordinary image) and the fluorescence image (specifically, the pseudo color image of the fluorescence image), which have been superimposed one upon the other by the display image processing unit 150.

A light guide 101, a CCD cable 102, and an image fiber 103 extend in the endoscope 100 up to a leading end of the endoscope 100. An illuminating lens 104 is located at a leading end of the light guide 101, i.e. at the leading end of the endoscope 100. An objective lens 105 is located at a leading end of the CCD cable 102, i.e. at the leading end of the endoscope 100. The image fiber 103 is constituted of glass fibers, and a converging lens 106 is located at a leading end of the image fiber 103. A CCD image sensor 108 is connected to the leading end of the CCD cable 102. A mosaic filter 107, which comprises fine band-pass filters arrayed in a mosaic form, is combined with the CCD image sensor 108. Also, a prism 109 is mounted on the CCD image sensor 108.

The mosaic filter 107 is a complementary color type of filter, which is constituted of color filters having colors acting as complementary colors with respect to the three primary colors. Each of the color filters of the mosaic filter 107 corresponds to one of pixels in the CCD image sensor 108.

The light guide 101 comprises a white light guide 101*a*, which is constituted of a compound glass fiber, and an excitation light guide 101*b*, which is constituted of a quartz glass fiber. The white light guide 101*a* and the excitation light guide 101b are bundled together in a cable-like form to constitute the light guide 101. The white light guide 101a and the excitation light guide 101b are connected to the illuminating unit 110. A tail end of the CCD cable 102 is connected to the ordinary image processing unit 140. A tail end of the image fiber 103 is connected to the fluorescence imaging unit 120.

The illuminating unit 110 comprises a white light source 111 for producing white light L1, which is used when an ordinary image is to be displayed, and an electric power source 112, which is electrically connected to the white light source 111. The illuminating unit 110 also comprises a GaN type of semiconductor laser 114 for producing excitation light L3, which is used when a fluorescence image is to be displayed, and an electric power source 115, which is electrically connected to the GaN type of semiconductor laser 114.

The fluorescence imaging unit 120 comprises an excitation light cut-off filter 121 for filtering out light, which has wavelengths falling within a wavelength region of at most 430 nm in the vicinity of the wavelength of the excitation light L3, from fluorescence L4 having passed through the image fiber 103. The fluorescence imaging unit 120 also comprises a CCD image sensor 125, which is constituted of a cooled, back exposure type of CCD image sensor. The CCD image sensor 125 is combined with a mosaic filter 123, which comprises two kinds of band-pass filters combined with each other in a mosaic-like form.

As illustrated in FIG. 3, the mosaic filter 123 is constituted of yellow filters 124a, 124a, . . . and blank areas 124b, 124b, . . . , which are arrayed alternately. The yellow filters 124a, 124a, . . . are band-pass filters, which transmit only light having wavelengths falling within a wavelength region (a) of at least 510 nm illustrated in FIG. 2. The blank areas 124b, 124b, . . . transmit light having wavelengths falling within an entire measurement wavelength region (b) illustrated in FIG. 2. Each of the yellow filters 124a, 124a, . . . and the blank areas 124b, 124b, . . . corresponds to one of pixels in the CCD image sensor 125.

The fluorescence image processing unit 130 comprises a signal processing circuit 131 for forming pseudo color image signals from the fluorescence image, which has been detected by the CCD image sensor 125. The fluorescence image processing unit 130 also comprises an analog-to-digital converting circuit 132 for digitizing the pseudo color image signals, which have been obtained from the signal processing circuit 131. The fluorescence image processing unit 130 further comprises a fluorescence image memory 133 for storing the digital pseudo color image signals, which have been obtained from the analog-to-digital converting circuit 132. The fluorescence image processing unit 130 still further comprises a digital-to-analog converting circuit 134 for performing digital-to-analog conversion on the pseudo color image signals, which have been received from the fluorescence image memory 133. The fluorescence image processing unit 130 also comprises a fluorescence image encoder 135 for transforming the pseudo color image signals, which have been received from the digital-to-analog converting circuit 134, into video signals.

As illustrated in FIG. 4, the signal processing circuit 131 comprises a process circuit 136 for performing sampling, clamping, blanking, amplification, and the like, on the signals having been obtained from the CCD image sensor 125. The signal processing circuit 131 also comprises a complementary color-to-primary color matrix operation circuit 137 for calculating the signal intensity of the fluorescence components of the fluorescence, which fluorescence components have wavelengths falling within the blue wavelength region, from the signal intensity of the fluorescence components of the fluorescence, which fluorescence components have passed through the yellow filters 124a, 124a, . . . , and the signal intensity of the fluorescence components of the fluorescence, which fluorescence components have passed through the blank areas 124b, 124b, . . . . The signal processing circuit 131 further comprises an image signal matrix operation circuit 138 for forming the pseudo color image signals from the signal intensity of the fluorescence components of the fluorescence, which fluorescence components have wavelengths falling within the blue wavelength region, and the signal intensity of the fluorescence components of the fluorescence, which fluorescence components have wavelengths falling within the entire measurement wavelength region.

The ordinary image processing unit 140 comprises a signal processing circuit 141 for forming color image signals from the ordinary image, which has been detected by the CCD image sensor 108. The ordinary image processing unit 140 also comprises an analog-to-digital converting circuit 142 for digitizing the color image signals, which have been obtained from the signal processing circuit 141. The ordinary image processing unit 140 further comprises an ordinary image memory 143 for storing the digital color image signals, which have been obtained from the analog-to-digital converting circuit 142. The ordinary image processing unit 140 still further comprises a digital-to-analog converting circuit 144 for performing digital-to-analog conversion on the color image signals, which have been received from the ordinary image memory 143. The ordinary image processing unit 140 also comprises an ordinary image encoder 145 for transforming the color image signals, which have been received from the digital-to-analog converting circuit 144, into video signals.

The display image processing unit 150 comprises a superimposer 151 for superimposing the pseudo color image signals, which have been received from the fluorescence image encoder 135, and the color image signals, which have been received from the ordinary image encoder 145, one upon the other, and feeding out the thus obtained image signals as the display signals. The display image processing unit 150 also comprises an RGB decoder 152 for transforming the display signals, which are the video signals, into R, G, and B display signals.

How the endoscope system, in which the first embodiment of the apparatus for displaying a fluorescence image in accordance with the present invention is employed, operates will be described hereinbelow. Firstly, how the endoscope system operates when an ordinary image is to be displayed will be described hereinbelow.

When an ordinary image is to be displayed, the electric power source 112 for the white light source 111 is driven in accordance with a control signal fed from the controller 160, and the white light L1 is produced by the white light source 111. The white light L1 passes through a lens 113 and impinges upon the white light guide 101a. The white light L1 is guided through the white light guide 101a to the leading end of the endoscope 100, passes through the illuminating lens 104, and is irradiated to a measuring site 10. The white light L1 is reflected as reflected light L2 from the measuring site 10. The reflected light L2 is converged by the objective lens 105 and reflected by the prism 109. The reflected light L2 then passes through the mosaic filter 107, is received by the CCD image sensor 108, and is photoelectrically converted into electric signals.

In the signal processing circuit 141, the processes, such as correlative double sampling, clamping, blanking, and amplification, are performed on the signals having been obtained from the CCD image sensor 108. Thereafter, the resulting signals are subjected to Y/C separation for separating a luminance signal and chrominance signals from one another. Thereafter, Y signal processing is performed, and a luminance signal Y1 is calculated. Also, complementary color signals, which have been separated from one another by the mosaic filter 107 combined with the CCD image sensor 108, are transformed into primary color signals (with complementary color-to-primary color transform). From the thus obtained primary color signals, color difference signals R1−Y1 and B1−Y1 are calculated with color difference matrix transform according to an NTSC method.

The color image signals (i.e., the luminance signal Y1 and the color difference signals R1−Y1 and B1−Y1), which are made up of color image signal components corresponding to respective pixels and have been obtained from the signal processing circuit 141, are digitized by the analog-to-digital converting circuit 142. The thus obtained luminance signal Y1 is stored in a luminance signal storage area of the ordinary image memory 143. The color difference signals R1−Y1 and B1−Y1 are stored in color difference signal storage areas of the ordinary image memory 143.

In accordance with a display timing, the color image signals (i.e., the luminance signal Y1 and the color difference signals R1−Y1 and B1−Y1) having been stored in the ordinary image memory 143 are subjected to the digital-to-analog conversion in the digital-to-analog converting circuit 144 and transformed by the ordinary image encoder 145 into predetermined video signals. The thus obtained video signals are fed into the superimposer 151 and superimposed upon the pseudo color image signals, which are obtained in the manner described later. The superimposed video signals are fed into the monitor 170 and the RGB decoder 152. How the monitor 170 and the RGB decoder 152 operate will be described later.

How the endoscope system, in which the first embodiment of the apparatus for displaying a fluorescence image in accordance with the present invention is employed, operates when a fluorescence image is to be displayed will be described hereinbelow.

When a fluorescence image is to be displayed, the electric power source 115 for the GaN type of semiconductor laser 114 is driven in accordance with a control signal fed from the controller 160, and the excitation light L3 having a wavelength of 410 nm is produced by the GaN type of semiconductor laser 114. The excitation light L3 passes through a lens 116 and impinges upon the excitation light guide 101b. The excitation light L3 is guided through the excitation light guide 101b to the leading end of the endoscope 100, passes through the illuminating lens 104, and is irradiated to the measuring site 10.

When the measuring site 10 is exposed to the excitation light L3, the fluorescence L4 is produced from the measuring site 10. The fluorescence L4 is converged by the converging lens 106 and impinges upon the leading end of the image fiber 103. The fluorescence L4 then passes through the image fiber 103 and impinges upon the excitation light cut-off filter 121 of the fluorescence imaging unit 120.

Thereafter, the fluorescence L4 is converged by a lens 122 and passes through the mosaic filter 123, which is combined with the CCD image sensor 125. In this manner, an image of the fluorescence L4 is formed on the CCD image sensor 125. Specifically, with the photoelectric conversion performed by the CCD image sensor 125, the image of the fluorescence L4 is converted into electric signals in accordance with the intensity of the fluorescence L4.

In the process circuit 136 of the signal processing circuit 131, the processes, such as correlative double sampling, clamping, blanking, and amplification, are performed on the signals having been obtained from the CCD image sensor 125. The signals having been obtained from the processes are fed as two-dimensional signals into the complementary color-to-primary color matrix operation circuit 137. Thereafter, in the complementary color-to-primary color matrix operation circuit 137, a signal intensity B2 of the fluorescence components of the fluorescence L4, which fluorescence components have wavelengths falling within the blue wavelength region, is calculated for each pixel in the manner described below. Specifically, matrix operations with Formula (1) shown below are performed by utilizing a signal intensity Ye2 of the fluorescence components, which have wavelengths falling within the yellow wavelength region (i.e., green+red) and have passed through the yellow filters 124a, 124a, . . . , and a signal intensity W2 of the fluorescence components, which have wavelengths falling within the entire measurement wavelength region and have passed through the blank areas 124b, 124b, . . . . Each of the matrix operations is performed by utilizing the signal intensities corresponding to pixels adjacent to each pixel.

$$B2 = [1, -1] \begin{bmatrix} W2 \\ Ye2 \end{bmatrix} \quad (1)$$

More specifically, the signal intensity B2 is calculated with the formula shown below.

$$B2 = W2 - Ye2$$

Further, in the image signal matrix operation circuit 138, color difference matrix operations according to the NTSC method are performed by utilizing the signal intensity B2 and the signal intensity W2. In this manner, a pseudo luminance signal Y2 and pseudo color difference signals R2−Y2 and B2−Y2, which act as the pseudo color image signals, are calculated with matrix operations represented by Formula (2) shown below.

$$\begin{bmatrix} Y2 \\ R2-Y2 \\ B2-Y2 \end{bmatrix} = \begin{bmatrix} a1 & a2 \\ b1 & b2 \\ c1 & c3 \end{bmatrix} \begin{bmatrix} W2 \\ B2 \end{bmatrix} \quad (2)$$

Therefore, the pseudo luminance signal Y2 and the pseudo color difference signals R2−Y2 and B2−Y2 are calculated with the formulas shown below.

$$Y2 = a1 \cdot W2 + a2 \cdot B2$$

$$R2 - Y2 = b1 \cdot W2 + b2 \cdot B2$$

$$B2 - Y2 = c1 \cdot W2 + c2 \cdot B2$$

The pseudo color image signals (i.e., the pseudo luminance signal Y2 and the pseudo color difference signals R2−Y2 and B2−Y2), which are made up of pseudo color image signal components corresponding to respective pixels and have been obtained from the signal processing circuit 131, are digitized by the analog-to-digital converting circuit 132. The thus obtained pseudo luminance signal Y2 is stored in a luminance signal storage area of the fluorescence image memory 133. Also, the thus obtained pseudo color difference signals R2–Y2 and B2–Y2 are stored in color difference signal storage areas of the fluorescence image memory 133. In accordance with the display timing, the pseudo color image signals (i.e., the pseudo luminance signal Y2 and the pseudo color difference signals R2–Y2 and B2–Y2) having been stored in the fluorescence image memory 133 are subjected to the digital-to-analog conversion in the digital-to-analog converting circuit 134 and transformed by the fluorescence image encoder 135 into predetermined video signals. The thus obtained video signals are fed from the fluorescence image encoder 135 into the superimposer 151. In the superimposer 151, the pseudo color image signals are superimposed upon the color image signals (i.e., the luminance signal Y1 and the color difference signals R1–Y1 and B1–Y1), which represent the ordinary image and have been received from the ordinary image encoder 145. The thus obtained video signals are fed into the monitor 170 and the RGB decoder 152.

The monitor 170 transforms the color image signals and the pseudo color image signals, which have been received as the video signals, and reproduces an ordinary image 30 and a fluorescence image 31 from the image signals having been obtained from the transform. The fluorescence image 31 is displayed with a pseudo color, such that the display color varies in accordance with the ratio between the signal intensity W2 of the fluorescence components, which have wavelengths falling within the entire measurement wavelength region, and the signal intensity B2 of the fluorescence components, which have wavelengths falling within the blue wavelength region. The tint of the pseudo color of the fluorescence image 31 is determined by the coefficients (a1, a2, b1, b2, c1, and c2) in the matrix operation formulas employed in the image signal matrix operation circuit 138.

The coefficients described above should preferably be selected such that the difference between the display color for the fluorescence, which has been produced from the normal tissues, and the display color for the fluorescence, which has been produced from the diseased tissues, may be clear. For example, the pseudo color may be displayed by selecting the coefficients such that the fluorescence, which has been produced from the normal tissues, may be displayed in white, and the fluorescence, which has been produced from the diseased tissues, may be displayed in pink or in one of other colors. In such cases, the person, who sees the displayed image, is capable of easily recognizing the state of the diseased tissues.

In the RGB decoder 152, the color signals R, G, and B representing the ordinary image and the color signals R, G, and B representing the fluorescence image are inversely transformed from the color image signals and the pseudo color image signals, which have been superimposed one upon the other. The color signals R, G, and B are fed into a device (not shown) capable of directly receiving the color signals, such as a printer or an image processing unit.

The series of operations described above are controlled by the controller 160 and are performed in accordance with a timing chart illustrated in FIG. 5. As illustrated in FIG. 5, the irradiation of the white light L1 and the exposure of the CCD image sensor 108 to the reflected light L2 are performed synchronously every 1/30 second. The irradiation of the excitation light L3 and the exposure of the CCD image sensor 125 to the fluorescence L4 are performed during a period, in which the irradiation of the white light L1 is ceased, i.e. during a period corresponding to a vertical blanking period in a television system. Therefore, the detection of the ordinary image is not obstructed by the detection of the fluorescence image. Also, since each of the ordinary image and the fluorescence image is detected every 1/30 second, the ordinary image 30 and the fluorescence image 31 are displayed on the monitor 170 as dynamic images, which are updated every 1/30 second.

As described above, with the endoscope system, in which the first embodiment of the apparatus for displaying a fluorescence image in accordance with the present invention is employed, the signal intensity W2 of the entire measurement wavelength region and the signal intensity Ye2 of the wavelength region of at least 510 nm are detected from the fluorescence L4, which is produced from the measuring site 10 when the measuring site 10 is exposed to the excitation light L3. Also, the signal intensity B2 of the blue wavelength region of at most 510 nm is calculated from the signal intensity W2 and the signal intensity Ye2. The display color in accordance with the ratio between the signal intensity W2 and the signal intensity B2 is displayed by the utilization of an additive color mixture process. Therefore, the efficiency, with which the fluorescence L4 having been produced from the measuring site 10 is utilized, is capable of being enhanced. Accordingly, adverse effects of noise are capable of being reduced, and the signal-to-noise ratio of the displayed fluorescence image is capable of being kept high.

Further, the endoscope system, in which the first embodiment of the apparatus for displaying a fluorescence image in accordance with the present invention is employed, is provided with the mosaic filter 123 provided with the blank areas 124b, 124b, . . . , which transmit the fluorescence components having wavelength falling within the entire measurement wavelength region. Therefore, the fluorescence L4 having been produced from the measuring site 10 is capable of being utilized most efficiently, and the signal-to-noise ratio of the displayed fluorescence image is capable of being enhanced even further. Furthermore, the signal intensities of the respective wavelength regions are capable of being detected simultaneously, and the signal intensity of the desired wavelength region is capable of being obtained in a real time mode. Therefore, the reliability of the displayed fluorescence image is capable of being enhanced.

In the endoscope system, in which the first embodiment of the apparatus for displaying a fluorescence image in accordance with the present invention is employed, the mosaic filter 123 is constituted of the yellow filters 124a, 124a, . . . , which transmit only the fluorescence components having wavelengths falling within the wavelength region of at least 510 nm, and the blank areas 124b, 124b, . . . , which transmit the fluorescence components having wavelengths falling within the entire measurement wavelength region. The mosaic filter 123 is combined with the CCD image sensor 125. With the CCD image sensor 125, the signal intensity Ye2 of the fluorescence components, which have wavelengths falling within the wavelength region of at least 510 nm, and the signal intensity W2 of the fluorescence components, which have wavelengths falling within the entire measurement wavelength region, are detected. Also, the signal intensity B2 of the fluorescence components, which have wavelengths falling within the blue wavelength region of at most 510 nm, is calculated from the signal intensity Ye2 and the signal intensity W2. Further, the pseudo color image in accordance with the ratio between the signal intensity B2 of the blue wavelength region and the signal intensity W2 of the entire measurement wavelength region is displayed. Alternatively, in a modification of the first embodiment, the mosaic filter 123 may be replaced by a mosaic filter constituted of cyan filters, which transmit only the fluorescence components having wavelengths falling within a wavelength region of at most 600 nm, and the blank areas, which transmit the fluorescence components having wavelengths falling within the entire measurement wavelength region. In such cases, with a CCD image sensor combined with the mosaic filter, a signal intensity of the wavelength region of at most 600 nm and the signal intensity of the entire measurement wavelength region may be detected, and a signal intensity of a red wavelength region of at least 600 nm may be calculated from the two detected signal intensities. Also, a pseudo color image in accordance with the ratio between the signal intensity of the red wavelength region and signal intensity of the entire measurement wavelength region may be displayed.

The ratio between the signal intensity of the red wavelength region and signal intensity of the entire measurement wavelength region varies for the fluorescence produced from the normal tissues and the fluorescence produced from the diseased tissues. Therefore, with the modification of the first embodiment, the same effects as those with the first embodiment are capable of being obtained.

Figure 6:
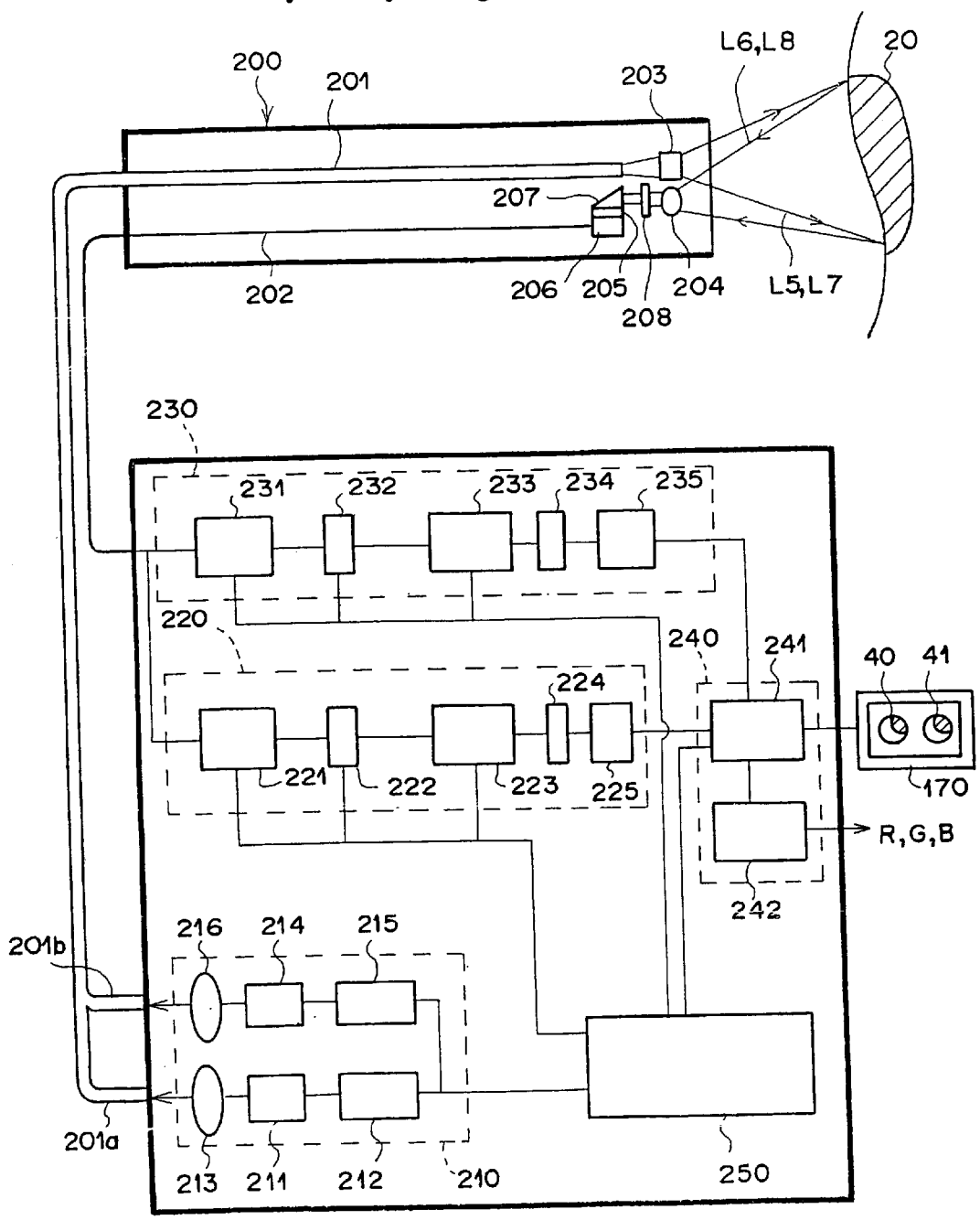
FIG. 6 is a schematic view showing an endoscope system, in which a second embodiment of the apparatus for displaying a fluorescence image in accordance with the present invention is employed.
Figure 7:
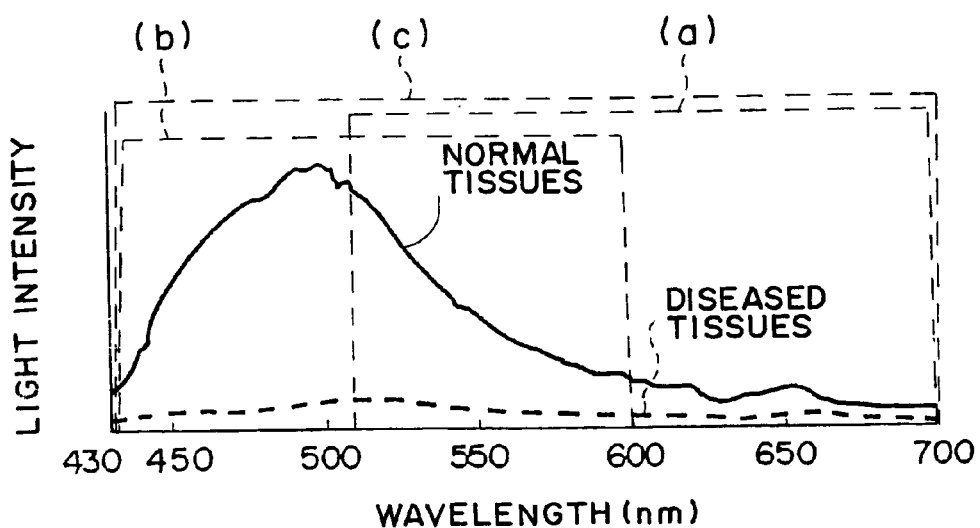
FIG. 7 is a graph showing transmission wavelength regions of band-pass filters constituting a mosaic filter employed in the endoscope system, in which the second embodiment of the apparatus for displaying a fluorescence image in accordance with the present invention is employed.

An endoscope system, in which a second embodiment of the apparatus for displaying a fluorescence image in accordance with the present invention is employed, will be described hereinbelow with reference to FIG. 6 to FIG. 9. FIG. 6 is a schematic view showing the endoscope system, in which the second embodiment of the apparatus for displaying a fluorescence image in accordance with the present invention is employed. In the endoscope system, in which the second embodiment of the apparatus for displaying a fluorescence image in accordance with the present invention is employed, excitation light is irradiated to a measuring site in a living body. Fluorescence produced from the measuring site is received by a CCD image sensor, which is located at a leading end of an endoscope and is utilized also for detecting an ordinary image. In this manner, a detected fluorescence image is displayed on the monitor.

The endoscope system, in which the second embodiment of the apparatus for displaying fluorescence information in accordance with the present invention is employed, comprises an endoscope 200 to be inserted into a region of a patient, which region is considered as being a diseased part, and an illuminating unit 210 provided with light sources for producing white light L5, which is used when an ordinary image is to be displayed, and excitation light L7, which is used when a fluorescence image is to be displayed. The endoscope system also comprises a fluorescence image processing unit 220 for performing image processing for displaying a fluorescence image as a pseudo color image, and an ordinary image processing unit 230 for performing image processing for displaying an ordinary image as a color image. The endoscope system further comprises a display image processing unit 240 for superimposing the ordinary image and the fluorescence image one upon the other. The endoscope system still further comprises a controller 250, which is connected to the respective units and controls operation timings. The endoscope system also comprises the monitor 170 for displaying the display images, which have been superimposed one upon the other by the display image processing unit 240.

A light guide 201 and a CCD cable 202 extend in the endoscope 200 up to a leading end of the endoscope 200. An illuminating lens 203 is located at a leading end of the light guide 201, i.e. at the leading end of the endoscope 200. An objective lens 204 is located at a leading end of the CCD cable 202, i.e. at the leading end of the endoscope 200. A CCD image sensor 206, which is constituted of a cooled, back exposure type of CCD image sensor, is connected to the leading end of the CCD cable 202. A mosaic filter 205, which comprises fine band-pass filters arrayed in a mosaic form, is combined with the CCD image sensor 206. Also, a prism 207 is mounted on the CCD image sensor 206. An excitation light cut-off filter 208 for filtering out light, which has wavelengths falling within a wavelength region of at most 430 nm in the vicinity of the wavelength of the excitation light L7, is located between the prism 207 and the objective lens 204.

Figure 8:
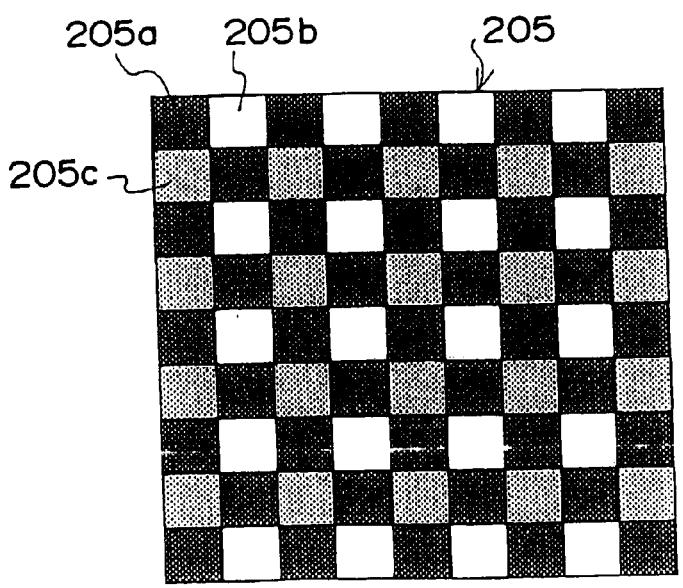
FIG. 8 is a schematic view showing the mosaic filter employed in the endoscope system, in which the second embodiment of the apparatus for displaying a fluorescence image in accordance with the present invention is employed.

As illustrated in FIG. 8, the mosaic filter 205 is constituted of yellow filters 205a, 205a, . . . , cyan filters 205b, 205b, . . . , and blank areas 205c, 205c, . . . , which are arrayed alternately. The yellow filters 205a, 205a, . . . are band-pass filters, which transmit only light having wavelengths falling within a wavelength region (a) of at least 510 nm illustrated in FIG. 7. The cyan filters 205b, 205b, . . . are band-pass filters, which transmit only light having wavelengths falling within a wavelength region (b) of at most 600 nm illustrated in FIG. 7. The blank areas 205c, 205c, . . . transmit light having wavelengths falling within an entire measurement wavelength region (c) illustrated in FIG. 7.

The light guide 201 comprises a white light guide 201a, which is constituted of a compound glass fiber, and an excitation light guide 201b, which is constituted of a quartz glass fiber. The white light guide 201a and the excitation light guide 201b are bundled together in a cable-like form to constitute the light guide 201. The white light guide 201a and the excitation light guide 201b are connected to the illuminating unit 210. A tail end of the CCD cable 202 is connected to the fluorescence image processing unit 220 and the ordinary image processing unit 230.

The illuminating unit 210 comprises a white light source 211 for producing the white light L5, which is used when an ordinary image is to be displayed, and an electric power source 212, which is electrically connected to the white light source 211. The illuminating unit 210 also comprises a GaN type of semiconductor laser 214 for producing the excitation light L7, which is used when a fluorescence image is to be displayed, and an electric power source 215, which is electrically connected to the GaN type of semiconductor laser 214.

The fluorescence image processing unit 220 comprises a signal processing circuit 221 for forming pseudo color image signals from a fluorescence image, which has been detected by the CCD image sensor 206. The fluorescence image processing unit 220 also comprises an analog-to-digital converting circuit 222 for digitizing the pseudo color image signals, which have been obtained from the signal processing circuit 221. The fluorescence image processing unit 220 further comprises a fluorescence image memory 223 for storing the digital pseudo color image signals, which have been obtained from the analog-to-digital converting circuit 222. The fluorescence image processing unit 220 still further comprises a digital-to-analog converting circuit 224 for performing digital-to-analog conversion on the pseudo color image signals, which have been received from the fluorescence image memory 223. The fluorescence image processing unit 220 also comprises a fluorescence image encoder 225 for transforming the pseudo color image signals, which have been received from the digital-to-analog converting circuit 224, into video signals.

As illustrated in FIG. 4, the signal processing circuit 221 comprises a process circuit 226 for performing image processing. The signal processing circuit 221 also comprises a complementary color-to-primary color matrix operation circuit 227 for calculating the signal intensity of the fluorescence components of the fluorescence, which fluorescence components have wavelengths falling within the blue wavelength region, and the signal intensity of the fluorescence components of the fluorescence, which fluorescence components have wavelengths falling within the red wavelength region, from the signal intensity of the fluorescence components of the fluorescence, which fluorescence components have passed through the yellow filters 205a, 205a, . . . , the signal intensity of the fluorescence components of the fluorescence, which fluorescence components have passed through the cyan filters 205b, 205b, . . . , and the signal intensity of the fluorescence components of the fluorescence, which fluorescence components have passed through the blank areas 205c, 205c, . . . . The signal processing circuit 221 further comprises an image signal matrix operation circuit 228 for forming the pseudo color image signals from the signal intensity of the fluorescence components of the fluorescence, which fluorescence components have wavelengths falling within the blue wavelength region, and the signal intensity of the fluorescence components of the fluorescence, which fluorescence components have wavelengths falling within the red wavelength region.

The ordinary image processing unit 230 comprises a signal processing circuit 231 for forming color image signals from the ordinary image, which has been detected by the CCD image sensor 206. The ordinary image processing unit 230 also comprises an analog-to-digital converting circuit 232 for digitizing the color image signals, which have been obtained from the signal processing circuit 231. The ordinary image processing unit 230 further comprises an ordinary image memory 233 for storing the digital color image signals, which have been obtained from the analog-to-digital converting circuit 232. The ordinary image processing unit 230 still further comprises a digital-to-analog converting circuit 234 for performing digital-to-analog conversion on the color image signals, which have been received from the ordinary image memory 233. The ordinary image processing unit 230 also comprises an ordinary image encoder 235 for transforming the color image signals, which have been received from the digital-to-analog converting circuit 234, into video signals.

As illustrated in FIG. 4, the signal processing circuit 231 comprises a process circuit 236 for performing image processing. The signal processing circuit 231 also comprises a complementary color-to-primary color matrix operation circuit 237 for calculating the signal intensities of the three primary colors, i.e., the signal intensities of the blue wavelength region, the green wavelength region, and the red wavelength region, from the signal intensity of the light components, which have passed through the yellow filters 205a, 205a, . . . , the signal intensity of the light components, which have passed through the cyan filters 205b, 205b, . . . , and the signal intensity of the light components, which have passed through the blank areas 205c, 205c, . . . . The signal processing circuit 231 further comprises an image signal matrix operation circuit 238 for forming the color image signals from the signal intensities of the three primary colors.

How the endoscope system, in which the second embodiment of the apparatus for displaying a fluorescence image in accordance with the present invention is employed, operates will be described hereinbelow. Firstly, how the endoscope system operates when an ordinary image is to be displayed will be described hereinbelow.

When an ordinary image is to be displayed, the electric power source 212 for the white light source 211 is driven in accordance with a control signal fed from the controller 250, and the white light L5 is produced by the white light source 211. The white light L5 passes through a lens 213 and impinges upon the white light guide 201a. The white light L5 is guided through the white light guide 201a to the leading end of the endoscope 200, passes through the illuminating lens 203, and is irradiated to a measuring site 20. The white light L5 is reflected as reflected light L6 from the measuring site 20. The reflected light L6 is converged by the objective lens 204, passes through the excitation light cut-off filter 208, and is reflected by the prism 207. The reflected light L6 then passes through the mosaic filter 205 and is received by the CCD image sensor 206.

In the process circuit 236 of the signal processing circuit 231, the processes are performed on the signals having been obtained from the CCD image sensor 206. Thereafter, in the complementary color-to-primary color matrix operation circuit 237, a signal intensity B3 of the light components of the reflected light L6, which light components have wavelengths falling within the blue wavelength region, a signal intensity G3 of the light components of the reflected light L6, which light components have wavelengths falling within the green wavelength region, and a signal intensity R3 of the light components of the reflected light L6, which light components have wavelengths falling within the red wavelength region, are calculated for each pixel in the manner described below. Specifically, matrix operations with Formula (3) shown below are performed by utilizing a signal intensity Ye3 of the light components, which have wavelengths falling within the yellow wavelength region (i.e., green+red) and have passed through the yellow filters 205a, 205a, . . . , a signal intensity Cy3 of the light components, which have wavelengths falling within the cyan wavelength region (i.e., blue+green) and have passed through the cyan filters 205b, 205b, . . . , and a signal intensity W3 of the light components, which have wavelengths falling within the entire measurement wavelength region and have passed through the blank areas 205c, 205c, . . . . Each of the matrix operations is performed by utilizing the image signal components corresponding to pixels adjacent to each pixel.

$$\begin{bmatrix} R3 \\ G3 \\ B3 \end{bmatrix} = \begin{bmatrix} 1 & 0 & -1 \\ -1 & 1 & 1 \\ 1 & -1 & 0 \end{bmatrix} \begin{bmatrix} W3 \\ Ye3 \\ Cy3 \end{bmatrix} \quad (3)$$

More specifically, the calculations are made with the formula shown below.

$R3=W3-Cy3$ $G3=-W3+Ye3+Cy3$ $B3=W3-Ye3$

Further, in the image signal matrix operation circuit 238, matrix operations according to the NTSC method are performed by utilizing the signal intensity B3 of the light components, which have wavelengths falling within the blue wavelength region, the signal intensity G3 of the light components, which have wavelengths falling within the green wavelength region, and the signal intensity R3 of the light components, which have wavelengths falling within the red wavelength region. In this manner, a luminance signal Y3 and color difference signals R3−Y3 and B3−Y3, which act as the color image signals, are calculated with matrix operations represented by Formula (4) shown below.

$$\begin{bmatrix} Y3 \\ R3-Y3 \\ B3-Y3 \end{bmatrix} = \begin{bmatrix} 0.30 & 0.59 & 0.11 \\ 0.70 & -0.59 & -0.11 \\ -0.30 & -0.59 & 0.89 \end{bmatrix} \begin{bmatrix} R3 \\ G3 \\ B3 \end{bmatrix} \quad (4)$$

Specifically, the luminance signal Y3 and the color difference signals R3-Y3 and B3-Y3 are calculated with the formulas shown below.

$$Y3 = 0.30R3 + 0.59G3 + 0.11B3$$

$$R3 - Y3 = 0.70R3 - 0.59G3 - 0.11B3$$

$$B3 - Y3 = -0.30R3 - 0.59G3 + 0.89B3$$

The color image signals (i.e., the luminance signal Y3 and the color difference signals R3-Y3 and B3-Y3), which are made up of color image signal components corresponding to respective pixels and have been obtained from the signal processing circuit 231, are digitized by the analog-to-digital converting circuit 232. The thus obtained luminance signal Y3 is stored in a luminance signal storage area of the ordinary image memory 233. Also, the thus obtained color difference signals R3-Y3 and B3-Y3 are stored in color difference signal storage areas of the ordinary image memory 233. In accordance with the display timing, the color image signals having been stored in the ordinary image memory 233 are subjected to the digital-to-analog conversion in the digital-to-analog converting circuit 234 and transformed by the ordinary image encoder 235 into predetermined video signals. The thus obtained video signals are fed from the ordinary image encoder 235 into a superimposer 241. In the superimposer 241, the color image signals are superimposed upon the pseudo color image signals, which are formed in the manner described later. The superimposed image signals are fed into the monitor 170.

How the endoscope system, in which the second embodiment of the apparatus for displaying a fluorescence image in accordance with the present invention is employed, operates when a fluorescence image is to be displayed will be described hereinbelow.

When a fluorescence image is to be displayed, the electric power source 215 for the GaN type of semiconductor laser 214 is driven in accordance with a control signal fed from the controller 250, and the excitation light L7 having a wavelength of 410 nm is produced by the GaN type of semiconductor laser 214. The excitation light L7 passes through a lens 216 and impinges upon the excitation light guide 201b. The excitation light L7 is guided through the excitation light guide 201b to the leading end of the endoscope 200, passes through the illuminating lens 203, and is irradiated to the measuring site 20.

When the measuring site 20 is exposed to the excitation light L7, fluorescence L8 is produced from the measuring site 20. The fluorescence L8 is converged by the converging lens 204, passes through the excitation light cut-off filter 208, and is then reflected by the prism 207. The fluorescence L8 then passes through the mosaic filter 205 and is received by the CCD image sensor 206.

Figure 9:
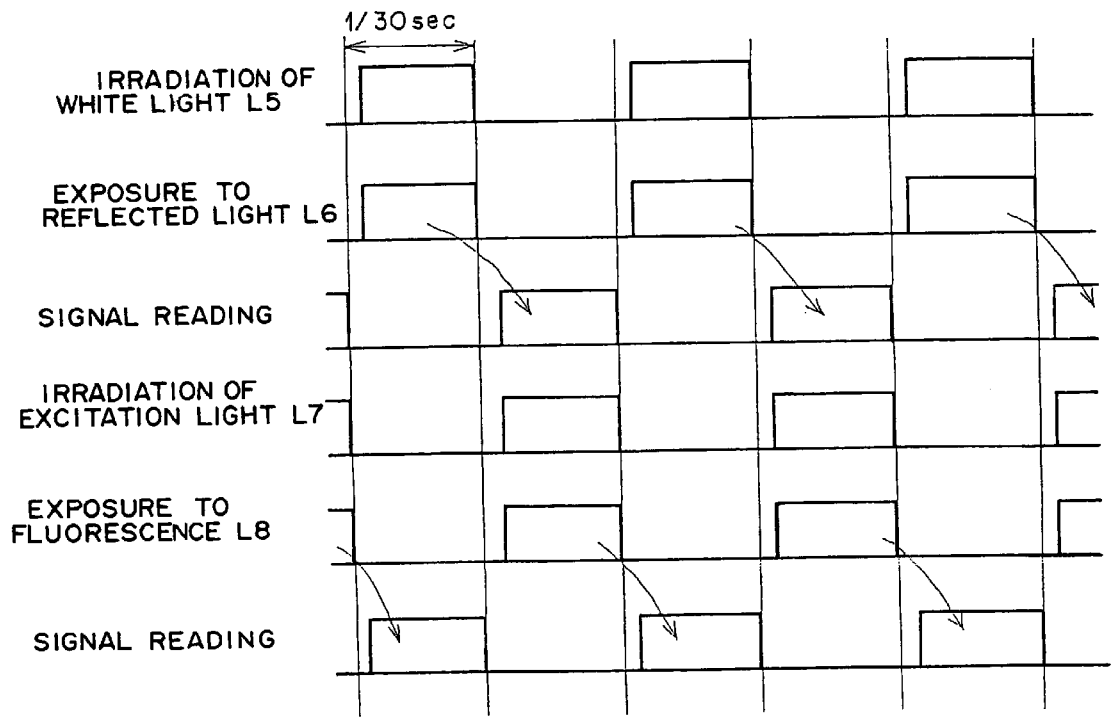
FIG. 9 is a timing chart employed in the endoscope system, in which the second embodiment of the apparatus for displaying a fluorescence image in accordance with the present invention is employed.

The timings, with which the imaging of the ordinary image with irradiation of the white light L5 and the imaging of the fluorescence image with irradiation of the excitation light L7 are performed, are performed in accordance with a timing chart illustrated in FIG. 9. As illustrated in FIG. 9, the operation for irradiating the white light L5 and exposing the CCD image sensor 206 to the ordinary image and the operation for irradiating the excitation light L7 and exposing the CCD image sensor 206 to the fluorescence image are performed alternately every 1/30 second. In cases where the ordinary image is detected, the output signals of the CCD image sensor 206 are fed into the signal processing circuit 231. In cases where the fluorescence image is detected, the output signals of the CCD image sensor 206 are fed into the signal processing circuit 221.

Therefore, each of the ordinary image and the fluorescence image is acquired every 1/15 second, and an ordinary image 40 and a fluorescence image 41 are displayed on the monitor 170 as dynamic images, which are updated every 1/15 second. The operation timings described above are controlled by the controller 250.

In the process circuit 226 of the signal processing circuit 221, the processes are performed on the signals having been obtained from the CCD image sensor 206. Thereafter, in the complementary color-to-primary color matrix operation circuit 227, a signal intensity B4 of the fluorescence components of the fluorescence L8, which fluorescence components have wavelengths falling within the blue wavelength region, and a signal intensity R4 of the fluorescence components of the fluorescence L8, which fluorescence components have wavelengths falling within the red wavelength region, are calculated for each pixel in the manner described below. Specifically, matrix operations with Formula (5) shown below are performed by utilizing a signal intensity Ye4 of the fluorescence components, which have wavelengths falling within the yellow wavelength region (i.e., green+red), a signal intensity Cy4 of the fluorescence components, which have wavelengths falling within the cyan wavelength region (i.e., blue+green), and a signal intensity W4 of the fluorescence components, which have wavelengths falling within the entire measurement wavelength region. Each of the matrix operations is performed by utilizing the signal intensities corresponding to pixels adjacent to each pixel.

$$\begin{bmatrix} R4 \\ B4 \end{bmatrix} = \begin{bmatrix} 1 & 0 & -1 \\ 1 & -1 & 0 \end{bmatrix} \begin{bmatrix} W4 \\ Ye4 \\ Cy4 \end{bmatrix} \quad (5)$$

More specifically, the calculations are made with the formula shown below.

$$R4 = W4 - Cy4$$

$$B4 = W4 - Ye4$$

Further, in the image signal matrix operation circuit 228, a pseudo luminance signal Y4 and pseudo color difference signals R4-Y4 and B4-Y4, which act as the pseudo color image signals, are calculated with matrix operations represented by Formula (6) shown below.

$$\begin{bmatrix} Y4 \\ R4-Y4 \\ B4-Y4 \end{bmatrix} = \begin{bmatrix} a3 & a4 \\ b3 & b4 \\ c3 & c4 \end{bmatrix} \begin{bmatrix} R4 \\ B4 \end{bmatrix} \quad (6)$$

Therefore, the pseudo luminance signal Y4 and the pseudo color difference signals R4-Y4 and B4-Y4 are calculated with the formulas shown below.

$$Y4 = a3 \cdot R4 + a4 \cdot B4$$

$$R4 - Y4 = b3 \cdot R4 + b4 \cdot B4$$

$$B4 - Y4 = c3 \cdot R4 + c4 \cdot B4$$

The pseudo color image signals (i.e., the pseudo luminance signal Y4 and the pseudo color difference signals R4–Y4 and B4–Y4), which are made up of color image signal components corresponding to respective pixels and have been obtained from the signal-processing circuit 221, are digitized by the analog-to-digital converting circuit 222. The thus obtained pseudo color image signals are stored in the fluorescence image memory 223. In accordance with the display timing, the pseudo color image signals having been stored in the fluorescence image memory 223 are subjected to the digital-to-analog conversion in the digital-to-analog converting circuit 224 and transformed by the fluorescence image encoder 225 into predetermined signals. The thus obtained signals are fed from the fluorescence image encoder 225 into the superimposer 241. In the superimposer 241, the pseudo color image signals are superimposed upon the color image signals representing the ordinary image (i.e., the luminance signal Y3 and the color difference signals R3–Y3 and B3–Y3), which have been obtained from the ordinary image memory 232. The superimposed image signals are fed into the monitor 170.

The monitor 170 transforms the color image signals and the pseudo color image signals into display signals and reproduces an ordinary image 40 and a fluorescence image 41 from the display signals. The fluorescence image 41 is displayed with a pseudo color, such that the display color varies in accordance with the ratio between the signal intensity R4 of the fluorescence components, which have wavelengths falling within the red wavelength region, and the signal intensity B4 of the fluorescence components, which have wavelengths falling within the blue wavelength region. The tint of the pseudo color of the fluorescence image 41 is determined by the coefficients (a3, a4, b3, b4, c3, and c4) in the matrix operation formulas employed in the image signal matrix operation circuit 228.

The coefficients described above should preferably be selected such that the difference between the display color for the fluorescence, which has been produced from the normal tissues, and the display color for the fluorescence, which has been produced from the diseased tissues, may be clear. For example, the pseudo color may be displayed by selecting the coefficients such that the fluorescence, which has been produced from the normal tissues, may be displayed in white, and the fluorescence, which has been produced from the diseased tissues, may be displayed in pink or in one of other colors. In such cases, the person, who sees the displayed image, is capable of easily recognizing the state of the diseased tissues.

As described above, with the endoscope system, in which the second embodiment of the apparatus for displaying a fluorescence image in accordance with the present invention is employed, the signal intensity W4 of the entire measurement wavelength region, the signal intensity Ye4 of the wavelength region of at least 510 nm, and the signal intensity Cy4 of the wavelength region of at most 600 nm are detected from the fluorescence L8, which is produced from the measuring site 20 when the measuring site 20 is exposed to the excitation light L7. Also, the signal intensity B4 of the blue wavelength region of at most 510 nm and the signal intensity R4 of the wavelength region of at least 600 nm are calculated from the signal intensity W4, the signal intensity Ye4 and the signal intensity Cy4. The display color in accordance with the ratio between the signal intensity B4 and the signal intensity R4 is displayed by the utilization of the additive color mixture process. Therefore, the efficiency, with which the fluorescence L8 having been produced from the measuring site 20 is utilized, is capable of being enhanced. Accordingly, the same effects as those with the first embodiment are capable of being obtained. Further, in the endoscope system, in which the second embodiment of the apparatus for displaying a fluorescence image in accordance with the present invention is employed, the signal intensity R4 of the red wavelength region, which signal intensity is comparatively weak and is apt to be affected by noise, is not detected by the CCD image sensor. Therefore, the adverse effects of noise are capable of being kept smaller, and the signal-to-noise ratio of the display image is capable of being kept higher than when the signal intensity R4 is detected in the conventional apparatus for displaying a fluorescence image.

Furthermore, with the endoscope system, in which the second embodiment of the apparatus for displaying a fluorescence image in accordance with the present invention is employed, the CCD image sensor for detecting the fluorescence image is utilized also as the CCD image sensor for detecting the ordinary image. Therefore, the production cost of the apparatus for displaying a fluorescence image is capable of being kept low.

In the first and second embodiments described above, the ratio between the signal intensities of the predetermined wavelength regions is displayed by the utilization of the additive color mixture process and is expressed as a change in tint of the display color. Alternatively, instead of the additive color mixture process being utilized, the detected signal intensities of the predetermined wavelength regions may be divided by each other, and the value obtained from the division may be displayed. As another alternative, the value obtained from the division may be compared with a reference value, which has been calculated previously from the fluorescence having been produced from the normal tissues and the fluorescence having been produced from the diseased tissues, and the results of the comparison may be displayed.

In such cases, instead of the pseudo luminance signal and the pseudo color difference signals being calculated from the signal intensities of the primary color signals in the complementary color-to-primary color matrix operation circuit of the signal processing circuit for the fluorescence image, the value obtained from the division of the signal intensities of the two primary color signals by each other may be calculated, and pseudo color image signals in accordance with the value obtained from the division may be formed. The pseudo color image signals may then be superimposed upon the color image signals representing the ordinary image.

Figure 10:
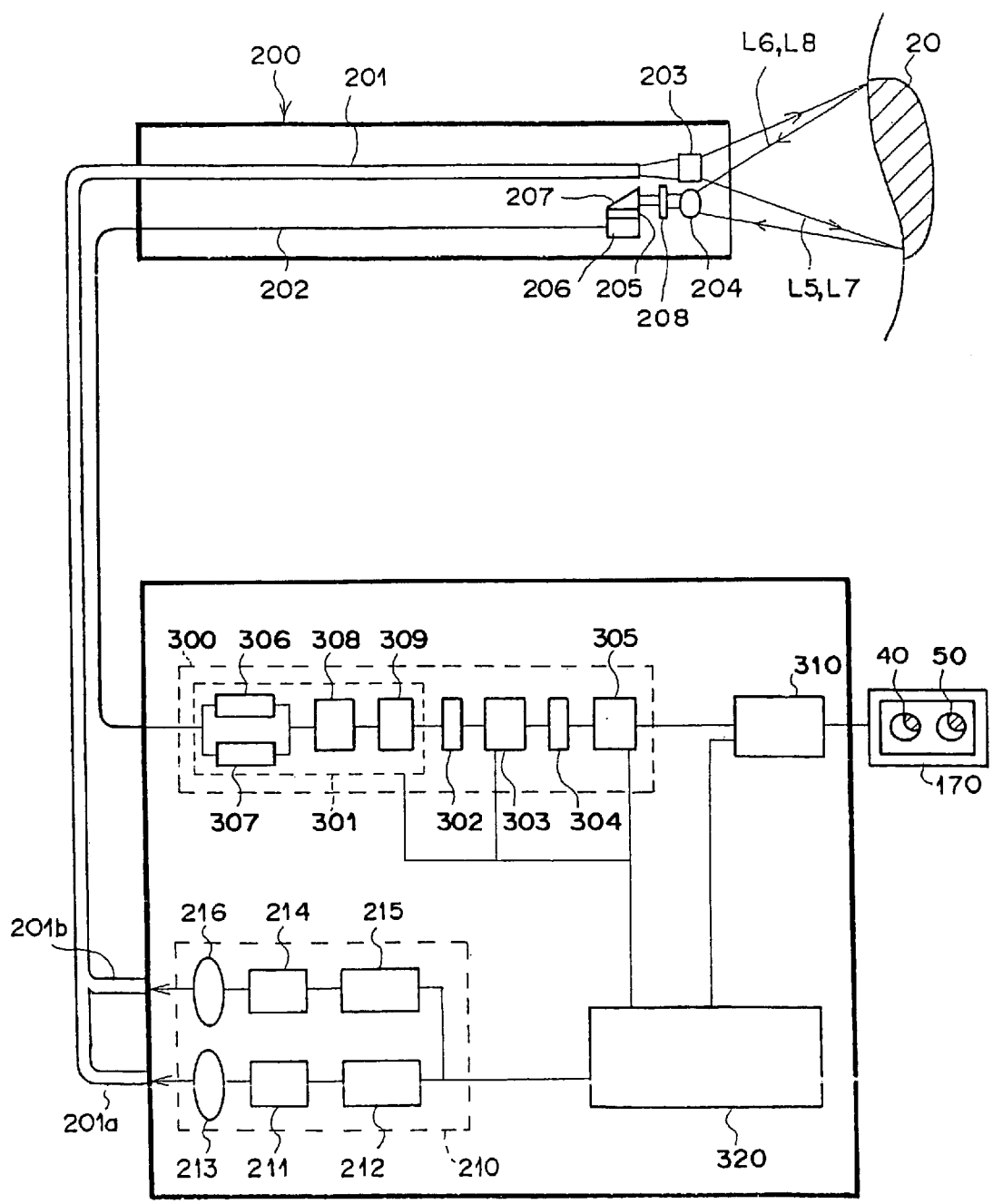
FIG. 10 is a schematic view showing an endoscope system, in which a third embodiment of the apparatus for displaying a fluorescence image in accordance with the present invention is employed.

An endoscope system, in which a third embodiment of the apparatus for displaying a fluorescence image in accordance with the present invention is employed, will be described hereinbelow with reference to FIG. 10. In FIG. 10, similar elements are numbered with the same reference numerals with respect to FIG. 6.

FIG. 10 is a schematic view showing the endoscope system, in which the third embodiment of the apparatus for displaying a fluorescence image in accordance with the present invention is employed. In the endoscope system, in which the third embodiment of the apparatus for displaying a fluorescence image in accordance with the present invention is employed, excitation light is irradiated to a measuring site in a living body. A fluorescence image of the measuring site is detected by a CCD image sensor, which is located at the leading end of the endoscope and is utilized also for detecting an ordinary image. In this manner, the detected fluorescence image is displayed as a color image on the monitor.

The endoscope system, in which the third embodiment of the apparatus for displaying fluorescence information in accordance with the present invention is employed, comprises the endoscope 200 to be inserted into a region of a patient, which region is considered as being a diseased part, and the illuminating unit 210 provided with the light sources for producing the white light L5, which is used when an ordinary image is to be displayed, and the excitation light L7, which is used when a fluorescence image is to be displayed. The endoscope system also comprises an image processing unit 300 for performing image processing for displaying a fluorescence image and an ordinary image. The endoscope system further comprises a superimposer 310 for superimposing the ordinary image and the fluorescence image one upon the other. The endoscope system still further comprises a controller 320, which is connected to the respective units and the superimposer 310 and controls operation timings. The endoscope system also comprises the monitor 170 for displaying the ordinary image and the fluorescence image as the color images.

The image processing unit 300 comprises a signal processing circuit 301 for forming color image signals from a fluorescence image and an ordinary image, which have been detected by the CCD image sensor 206. The image processing unit 300 also comprises an analog-to-digital converting circuit 302 for digitizing the color image signals, which have been obtained from the signal processing circuit 301. The image processing unit 300 further comprises an image memory 303 for storing the digital color image signals, which have been obtained from the analog-to-digital converting circuit 302. The image processing unit 300 still further comprises a digital-to-analog converting circuit 304 for performing digital-to-analog conversion on the color image signals, which have been received from the image memory 303. The image processing unit 300 also comprises an encoder 305 for transforming the color image signals, which have been received from the digital-to-analog converting circuit 304, into video signals.

The signal processing circuit 301 comprises an ordinary image process circuit 306 for performing the processes, such as double sampling, amplification, and clamping, on signals in cases where the ordinary image is detected by the CCD image sensor 206. The signal processing circuit 301 also comprises a fluorescence image process circuit 307 for performing the processes on signals in cases where the fluorescence image is detected by the CCD image sensor 206. The signal processing circuit 301 further comprises a complementary color-to-primary color matrix operation circuit 308 for calculating the signal intensities of the blue wavelength region, the green wavelength region, and the red wavelength region, from the signal intensity of the light components, which have passed through the yellow filters 205a, 205a, . . . , the signal intensity of the light components, which have passed through the cyan filters 205b, 205b, . . . , and the signal intensity of the light components, which have passed through the blank areas 205c, 205c, . . . . The signal processing circuit 301 further comprises an image signal matrix operation circuit 309 for forming the color image signals from the signal intensities having been calculated by the complementary color-to-primary color matrix operation circuit 308.

How the endoscope system, in which the third embodiment of the apparatus for displaying a fluorescence image in accordance with the present invention is employed, operates will be described hereinbelow. Firstly, how the endoscope system operates when an ordinary image is to be displayed will be described hereinbelow.

When an ordinary image is to be displayed, the electric power source 212 for the white light source 211 is driven in accordance with a control signal fed from the controller 320, and the white light L5 is produced by the white light source 211 and irradiated to the measuring site 20. The reflected light L6 of the white light L5 passes through the mosaic filter 205 and is received by the CCD image sensor 206.

In the ordinary image process circuit 306 of the signal processing circuit 301, the processes are performed on the signals having been obtained from the CCD image sensor 206. Thereafter, in the complementary color-to-primary color matrix operation circuit 308, in the same manner as that in the complementary color-to-primary color matrix operation circuit 237 of the signal processing circuit 231 shown in FIG. 6, the signal intensity B3 of the light components of the reflected light L6, which light components have wavelengths falling within the blue wavelength region, the signal intensity G3 of the light components of the reflected light L6, which light components have wavelengths falling within the green wavelength region, and the signal intensity R3 of the light components of the reflected light L6, which light components have wavelengths falling within the red wavelength region, are calculated for each pixel with the matrix operations by utilizing the signal intensity Ye3 of the light components, which have wavelengths falling within the yellow wavelength region (i.e., green+red), the signal intensity Cy3 of the light components, which have wavelengths falling within the cyan wavelength region (i.e., blue+green), and the signal intensity W3 of the light components, which have wavelengths falling within the entire measurement wavelength region. Each of the matrix operations is performed by utilizing the signal intensities corresponding to pixels adjacent to each pixel. Further, in the image signal matrix operation circuit 309, the matrix operations are performed by utilizing the signal intensities B3, G3, and R3 of the three primary colors. In this manner, the luminance signal Y3 and the color difference signals R3−Y3 and B3−Y3, which act as the color image signals according to the NTSC method, are calculated.

The color image signals (i.e., the luminance signal Y3 and the color difference signals R3−Y3 and B3−Y3), which are made up of color image signal components corresponding to respective pixels and have been obtained from the signal processing circuit 301, are digitized by the analog-to-digital converting circuit 302. The thus obtained color image signals are stored in an ordinary image storage area of the image memory 303. In accordance with the display timing, the color image signals, which represent the ordinary image and having been stored in the image memory 303, are subjected to the digital-to-analog conversion in the digital-to-analog converting circuit 304 and transformed by the encoder 305 into predetermined video signals. The thus obtained video signals are fed from the encoder 305 into the superimposer 310. In the superimposer 310, the color image signals are superimposed upon the color image signals, which represent the fluorescence image and are formed in the manner described later. The superimposed image signals are fed into the monitor 170.

How the endoscope system, in which the third embodiment of the apparatus for displaying a fluorescence image in accordance with the present invention is employed, operates when a fluorescence image is to be displayed will be described hereinbelow.

When a fluorescence image is to be displayed, the electric power source 215 for the GaN type of semiconductor laser 214 is driven in accordance with a control signal fed from the controller 320, and the excitation light L7 having a wavelength of 410 nm is produced by the GaN type of semiconductor laser 214. The excitation light L7 is irradiated to the measuring site 20.

When the measuring site 20 is exposed to the excitation light L7, fluorescence L8 is produced from the measuring site 20. The fluorescence L8 passes through the mosaic filter 205 and is received by the CCD image sensor 206.

As in the second embodiment described above, the timings, with which the imaging of the ordinary image with irradiation of the white light L5 and the imaging of the fluorescence image with irradiation of the excitation light L7 are performed, are controlled by the controller 320 and performed in accordance with the timing chart illustrated in FIG. 9. As illustrated in FIG. 9, the operation for irradiating the white light L5 and exposing the CCD image sensor 206 to the ordinary image and the operation for irradiating the excitation light L7 and exposing the CCD image sensor 206 to the fluorescence image are performed alternately every 1/30 second. In accordance with control signals given by the controller 320, the signals obtained from the detection of the ordinary image are fed into the ordinary image process circuit 306, and the signals obtained from the detection of the fluorescence image are fed into the fluorescence image process circuit 307.

Therefore, each of the ordinary image and the fluorescence image is acquired every 1/15 second, and the ordinary image 40 and a fluorescence image 50 are displayed on the monitor 170 as dynamic images, which are updated every 1/15 second.

In the fluorescence image process circuit 307 of the signal processing circuit 301, the processes are performed on the signals having been obtained from the CCD image sensor 206. Thereafter, as in cases where the ordinary image is detected, in the complementary color-to-primary color matrix operation circuit 308, a signal intensity B5 of the fluorescence components of the fluorescence L8, which fluorescence components have wavelengths falling within the blue wavelength region, a signal intensity G5 of the fluorescence components of the fluorescence L8, which fluorescence components have wavelengths falling within the green wavelength region, and a signal intensity R5 of the fluorescence components of the fluorescence L8, which fluorescence components have wavelengths falling within the red wavelength region, are calculated for each pixel with the matrix operations by utilizing a signal intensity Ye5 of the fluorescence components, which have wavelengths falling within the yellow wavelength region, a signal intensity Cy5 of the fluorescence components, which have wavelengths falling within the cyan wavelength region, and a signal intensity W5 of the fluorescence components, which have wavelengths falling within the entire measurement wavelength region. Further, in the image signal matrix operation circuit 309, the matrix operations according to the NTSC method are performed by utilizing the signal intensities B5, G5, and R5 of the three primary colors. In this manner, a luminance signal Y5 and color difference signals R5-Y5 and B5-Y5, which act as the color image signals, are calculated.

The color image signals (i.e., the luminance signal Y5 and the color difference signals R5-Y5 and B5-Y5), which are made up of color image signal components corresponding to respective pixels and have been obtained from the signal processing circuit 301, are digitized by the analog-to-digital converting circuit 302. The thus obtained color image signals are stored in a fluorescence image storage area of the image memory 303. In accordance with the display timing, the color image signals, which represent the fluorescence image and having been stored in the image memory 303, are subjected to the digital-to-analog conversion in the digital-to-analog converting circuit 304 and transformed by the encoder 305 into predetermined signals. The thus obtained signals are fed from the encoder 305 into the superimposer 310. In the superimposer 310, the color image signals are superimposed upon the color image signals representing the ordinary image (i.e., the luminance signal Y3 and the color difference signals R3-Y3 and B3-Y3), which have been received from the image memory 303. The superimposed image signals are fed into the monitor 170.

The monitor 170 transforms the color image signals representing the ordinary image and the color image signals representing the fluorescence image and displays the ordinary image 40 and the fluorescence image 50.

Therefore, in the fluorescence image 50, as in the cases of the ordinary image 40, the signal intensity B5 of the wavelength region of 430 nm to 510 nm is displayed as the color signal B, the signal intensity G5 of the wavelength region of 510 nm to 600 nm is displayed as the color signal G, and the signal intensity R5 of the wavelength region of 600 nm to 700 nm is displayed as the color signal R. In this manner, the fluorescence image 50 is displayed as an ordinarily formed color image. Accordingly, the display color with respect to the fluorescence produced from the normal tissues is cyan, and the display color with respect to the fluorescence produced from the diseased tissues is a color close to white. Thus the same effects as those with the second embodiment shown in FIG. 6 are capable of being obtained. Further, a fine difference between the signal intensities of wavelength regions of the fluorescence produced from the measuring site is capable of being displayed as a difference in tint.

In the third embodiment described above, as the coefficients in the matrix operations for transforming the three primary color signals B5, G5, and R5 into the color image signals in the image signal matrix operation circuit 309, the coefficients, which are utilized in ordinary matrix operations employed in the NTSC method, are employed. Alternatively, the coefficients in the matrix operations may be selected in different ways. In this manner, the tint corresponding to each signal intensity may be set arbitrarily.

Figure 11:
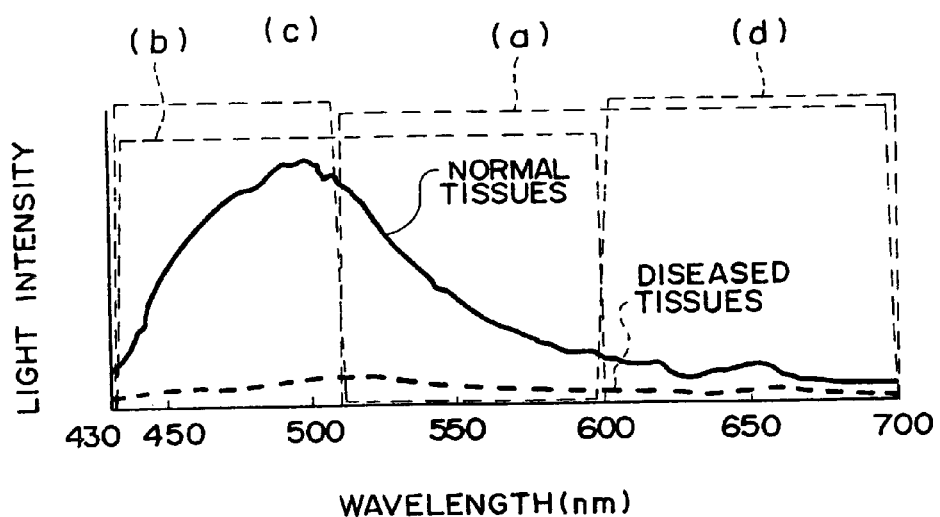
FIG. 11 is a graph showing transmission wavelength regions of band-pass filters constituting a mosaic filter employed in an endoscope system, in which a modification of the embodiments of the apparatus for displaying a fluorescence image in accordance with the present invention is employed.
Figure 12:
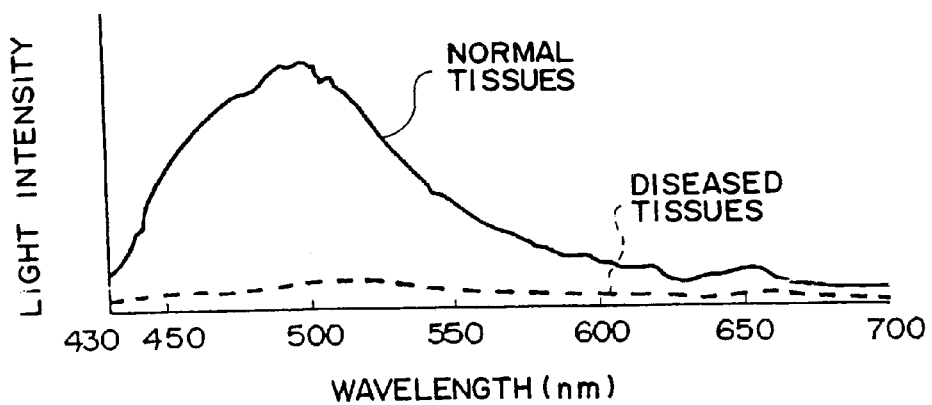
FIG. 12 is a graph showing spectral intensity distributions of fluorescence produced from normal tissues and fluorescence produced from diseased tissues.

In the endoscope systems described above, in which the embodiments of the apparatus for displaying a fluorescence image in accordance with the present invention are employed, the mosaic filter 123, which is constituted of the yellow filters 124a, 124a, . . . and the blank areas 124b, 124b, . . . , or the mosaic filter 205, which is constituted of the yellow filters 205a, 205a, . . . , the cyan filters 205b, 205b, . . . , and the blank areas 205c, 205c, . . . , is employed. Alternatively, as illustrated in FIG. 11, in a modification of the embodiments of the apparatus for displaying a fluorescence image in accordance with the present invention, in lieu of the mosaic filters described above, a mosaic filter may be employed, which is constituted of yellow filters for transmitting only light having wavelengths falling within a wavelength region (a) of at least 510 nm, cyan filters for transmitting only light having wavelengths falling within a wavelength region (b) of at most 600 nm, and magenta filters acting as band-pass filters for transmitting only light having wavelengths falling within a wavelength region (d) comprising a sub-region of at most 510 nm and a sub-region of at least 600 nm.

In the modification described above, wherein the blank areas for transmitting light having wavelengths falling within the entire measurement wavelength region are not provided, a signal intensity W' of the entire measurement wavelength region may be calculated with the formula shown below.

$$W' = \tfrac{1}{2}(Ye' + Cy' + Mg')$$

in which Ye' represents the signal intensity of the light components having passed through the yellow filters, Cy' represents the signal intensity of the light components having passed through the cyan filters, and Mg' represents the signal intensity of the light components having passed through the magenta filters.

Therefore, a signal intensity B' of the blue wavelength region, a signal intensity G' of the green wavelength region, and a signal intensity R' of the red wavelength region may be calculated with the formulas shown below.

$$B' = 1/2(-Ye' + Cy' + Mg')$$
$$G' = 1/2(Ye' + Cy' - Mg')$$
$$R' = 1/2(Ye' - Cy' + Mg')$$

Thereafter, pseudo color image signals and color image signals may be calculated from the thus calculated color signals, and a pseudo color image or a color image may thereby be displayed. In this manner, the same effects as those with the second or third embodiment described above are capable of being obtained.

Further, in the embodiments described above, the signal intensities of the respective wavelength regions are detected by use of the mosaic filter, which comprises a plurality of fine filter elements arrayed alternately in a two-dimensional plane. Alternatively, for example, a rotating filter, which comprises a plurality of filters larger than the CCD image sensor, may be located in front of the CCD image sensor. In such cases, the signal intensities of the respective wavelength regions are capable of being calculated successively. In such cases, since the signal intensity of a desired wavelength region is calculated from the signal intensities of the respective wavelength regions having been stored successively, the display image cannot be displayed on the real time mode. However, in such cases, the resolution is capable of being enhanced, and therefore a sharp display image is capable of being obtained as for a measuring site, at which little motion occurs.

In addition, all of the contents of Japanese Patent Application No. 11(1999)-366667 are incorporated into this specification by reference.

What is claimed is:

1. An apparatus for displaying a fluorescence image, comprising:
   i) excitation light irradiating means for irradiating excitation light to a measuring site in a living body, the excitation light causing the measuring site to produce fluorescence,
   ii) image information acquiring means for acquiring image information in accordance with a signal intensity of fluorescence components of the fluorescence having been produced from the measuring site exposed to the excitation light, which fluorescence components have wavelengths falling within at least one desired wavelength region, and
   iii) displaying means for displaying the acquired image information,
   wherein the image information acquiring means comprises:
      a) a complementary color filter for transmitting only fluorescence components of the fluorescence, which fluorescence components have wavelengths falling within a wavelength region acting as a complementary color with respect to the desired wavelength region,
      b) complementary color signal intensity detecting means for detecting a signal intensity of the fluorescence components of the fluorescence, which fluorescence components have passed through the complementary color filter,
      c) entire signal intensity detecting means for detecting a signal intensity of fluorescence components of the fluorescence, which fluorescence components have wavelengths falling within an entire measurement wavelength region of the fluorescence, and
      d) signal intensity calculating means for calculating the signal intensity of the fluorescence components of the fluorescence, which fluorescence components have wavelengths falling within the desired wavelength region, from the signal intensity, which has been detected by the complementary color signal intensity detecting means, and the signal intensity, which has been detected by the entire signal intensity detecting means.

2. An apparatus as defined in claim 1 wherein the entire signal intensity detecting means comprises an all-pass filter for transmitting the fluorescence components of the fluorescence, which fluorescence components have wavelengths falling within the entire measurement wavelength region of the fluorescence, and
   entire measurement signal intensity detecting means for detecting the signal intensity of the fluorescence components of the fluorescence, which fluorescence components have passed through the all-pass filter.

3. An apparatus as defined in claim 2 wherein a plurality of complementary color filters and a plurality of all-pass filters are arrayed alternately on a two-dimensional plane so as to constitute a mosaic filter.

4. An apparatus for displaying a fluorescence image, comprising:
   i) excitation light irradiating means for irradiating excitation light to a measuring site in a living body, the excitation light causing the measuring site to produce fluorescence,
   ii) image information acquiring means for acquiring image information in accordance with a signal intensity of fluorescence components of the fluorescence having been produced from the measuring site exposed to the excitation light, which fluorescence components have wavelengths falling within at least one desired wavelength region selected from among a blue wavelength region, a green wavelength region, and a red wavelength region, and
   iii) displaying means for displaying the acquired image information,
   wherein the image information acquiring means comprises:
      a) a yellow filter for transmitting only fluorescence components of the fluorescence, which fluorescence components have wavelengths falling within a yellow wavelength region acting as a complementary color with respect to the blue wavelength region,
      b) a magenta filter for transmitting only fluorescence components of the fluorescence, which fluorescence components have wavelengths falling within a magenta wavelength region acting as a complementary color with respect to the green wavelength region,
      c) a cyan filter for transmitting only fluorescence components of the fluorescence, which fluorescence components have wavelengths falling within a cyan wavelength region acting as a complementary color with respect to the red wavelength region, d) complementary color signal intensity detecting means for detecting a signal intensity of the fluorescence components of the fluorescence, which fluorescence components have passed through the yellow filter, a signal intensity of the fluorescence components of the fluorescence; which fluorescence components have passed through the magenta filter, and a signal intensity of the fluorescence components of the fluorescence, which fluorescence components have passed through the cyan filter, e) entire signal intensity calculating means for calculating a signal intensity of fluorescence components of the fluorescence, which fluorescence components have wavelengths falling within an entire measurement wavelength region of the fluorescence, from the signal intensity of the fluorescence components having wavelengths falling within the yellow wavelength region, the signal intensity of the fluorescence components having wavelengths falling within the magenta wavelength region, and the signal intensity of the fluorescence components having wavelengths falling within the cyan wavelength region, which signal intensities have been detected by the complementary color signal intensity detecting means, and f) signal intensity calculating means for calculating the signal intensity of the fluorescence components of the fluorescence, which fluorescence components have wavelengths falling within the desired wavelength region, from the signal intensities, which have been detected by the complementary color signal intensity detecting means, and the signal intensity of the fluorescence components having wavelengths falling within the entire measurement wavelength region of the fluorescence, which signal intensity has been calculated by the entire signal intensity calculating means.

5. An apparatus as defined in claim 4 wherein a plurality of yellow filters, a plurality of magenta filters, and a plurality of cyan filters are arrayed alternately on a two-dimensional plane so as to constitute a mosaic filter.

* * * * *